(12) United States Patent
Appella et al.

(10) Patent No.: US 7,329,775 B2
(45) Date of Patent: Feb. 12, 2008

(54) COMPOUNDS AND RELATED METHODS FOR MUTANT P53 REACTIVATION

(75) Inventors: Daniel H. Appella, Rockville, MD (US); Michael C. Myers, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/978,702

(22) Filed: Nov. 1, 2004

(65) Prior Publication Data
US 2005/0245616 A1 Nov. 3, 2005

Related U.S. Application Data

(60) Provisional application No. 60/515,828, filed on Oct. 30, 2003.

(51) Int. Cl.
*C07C 69/00* (2006.01)

(52) U.S. Cl. .................. 560/250; 560/129; 564/342

(58) Field of Classification Search ................ 560/250, 560/129; 564/342
See application file for complete search history.

(56) References Cited

U.S. PATENT DOCUMENTS 2,515,240 A * 7/1950 Long ......................... 564/342
2,562,107 A   7/1951 Long

FOREIGN PATENT DOCUMENTS

GB           664695     *   1/1952

OTHER PUBLICATIONS

Chemical Abstract 2205i, 1958.*

* cited by examiner

*Primary Examiner*—Shailendra Kumar
(74) *Attorney, Agent, or Firm*—Reinhart Boerner Van Deuren S.C.

(57) ABSTRACT

Ketoamine compounds and related methods for reactivation of tumor suppressor protein p53.

7 Claims, 9 Drawing Sheets

Saos-2 (null)　　　　Saos-2 (mtp53-281)

PRIMA-1

25 μM (All cells killed at 75 μM)

10 μM (All cells killed at 25 μM)
(No cells killed at 1 μM and lower)

D- or L-Serine

1. Boc₂O
2. TBSCl, Imidazole
3. MeNH(OMe), EDCl

22

1. $R^2MgX_2$ or $R^2Li$
2. TBAF
3. Alkylation or Acylation

4. TFA
5. Alkylation or Acylation $R^1$, $R^3$-$R^4$ = Alkyl or Acyl Group
$R^2$ = Aryl or Alkyl Group D- or L-Homoserine      D- or L-Diaminopropionic Acid      D- or L-Diaminobutyric Acid

COMPOUNDS AND RELATED METHODS FOR MUTANT P53 REACTIVATION

This application claims priority benefit from application Ser. No. 60/515,828 filed Oct. 30, 2003, the entirety of which is incorporated herein by reference.

The United States government has certain rights to this invention pursuant to Grant Nos. CA63230, CA71907 and CA21765 from the National Institutes of Health to Northwestern University.

BACKGROUND OF THE INVENTION

The protein p53 is an important tumor suppressor. Under normal conditions, cells do not contain high levels of this protein. If a healthy cell is damaged, p53 is expressed and its cellular level increases, followed by inhibition of cell growth or programmed cell death (apoptosis). In order to induce apoptosis, p53 must bind to a specific DNA sequence. Numerous studies have demonstrated that p53 plays a very important role in directing a cell to stop growing or to undergo apoptosis. Therefore, p53 has been recognized as one of the most important guardians in the body to prevent damaged cells from developing into tumors. In approximately 50% of human tumors, a mutated form of p53 (mutant p53) is present that is unable to bind target DNA sequences, allowing an unregulated growth and division of such tumor cells. Indeed, mutation of p53 is considered the most frequent genetic alteration occurring in human cancer. Further, tumors associated with mutant p53 are often more resistant to chemotherapy than tumors with wild-type p53.

However, once a mutant p53 protein regains the ability to bind DNA, the tumor suppressor activity is restored and apoptosis is induced, consequently killing the cancer cell. The potential for small organic molecules to reactivate mutant forms of this protein has created a revolutionary new strategy for attacking cancer. In tumor cells, mutant forms of p53 are commonly present at elevated levels compared to wild-type p53 in healthy cells. This imbalance offers the possibility of selectively killing cancer cells over healthy cells via reactivation of mutant p53, which could lead to medications without the devastating side effects often associated with conventional chemotherapy. In addition to potential clinical applications, the ability to reactivate mutant p53 has also generated a fundamentally new approach in biomedical research: the possibility of designing organic molecules to re-establish the normal functions of a mutated protein.

Random screenings of combinatorial libraries have identified a handful of small organic molecules that affect the activity of p53 (FIG. 1). One of these molecules (PFTA) inhibits the DNA binding activity of wild-type p53, while others (e.g., CP-31398, CP-257042, PRIMA-1) restore or reactivate the DNA-binding activity of mutant p53 proteins. Although each of these molecules is structurally very different, there are common features among them that indicate the types of molecules to target p53. For example, each of these molecules has one or more amine functional groups that convey a net cationic charge under aqueous or physiological conditions. Most of these compounds also have aromatic groups, suggesting that aromatic-aromatic interactions promote binding to p53. In compounds CP-31398 and CP-257042, aromatic portions of these molecules are similar to known compounds that intercalate between the bases of DNA (such as ethidium bromide and acridine). It has been suggested that these molecules restore DNA-binding activity to p53 by binding simultaneously to both DNA and p53. However, while intercalation of aromatic groups into DNA is a favorable process, aromatic intercalators can also have mutagenic properties and thus are not suitable motifs for further development.

Among the compounds in FIG. 1, PRIMA-1 is an interesting target: it lacks an aromatic group (and therefore should not intercalate into DNA), yet it still restores DNA-binding activity to mutant p53. Although detailed knowledge about the interactions of PRIMA-1 with p53 are not known, it most likely involves a positioning of cationic charge and hydrogen bonding groups into proper orientations for p53 protein binding. This binding event may somehow induce a conformational change in mutant p53 such that DNA binding is restored. Alternatively, PRIMA-1 could also interact with a different protein target that then affects p53. However, the chemistry en route to PRIMA-1 precludes most structural analogs. The synthesis of PRIMA-1 does not readily allow introduction of chemical modifications, limiting access to analogs that target different mutant forms of p53 or derivatives that probe the mechanism of action.

P53 reactivation has been an on-going concern in the art. As outlined above, new approaches in organic chemistry are needed to synthesize new molecules that interact with p53. By examining the activity of such novel compounds, structure-activity relationships can be determined that will provide crucial information for development of new medications and understanding the mechanism(s) of action. These results can provide important insights into p53 reactivation and possibly new cancer chemotherapies.

SUMMARY OF THE INVENTION

Figure 1:
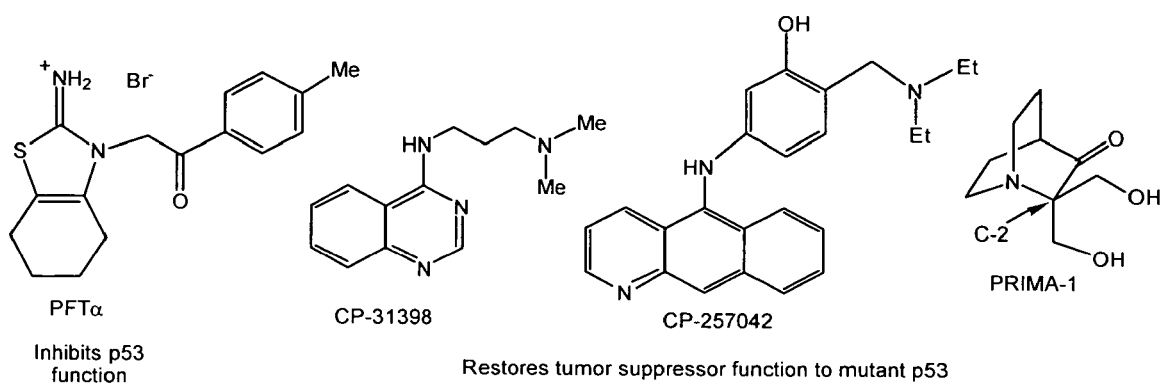
FIG. 1 shows several recently discovered organic molecules of the prior art that interact with mutant p53.

In light of the foregoing, it is an object of the present invention to provide a wide range of readily-synthesized compositions and/or methods for their use in the inhibition of tumor cell growth, reactivation of the tumor suppressor function of mutant p53 and/or examination of the related DNA binding mechanism of reactivated p53, thereby addressing various concerns of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more compounds or compositions capable of restoring wild-type DNA p53 binding capabilities to mutant p53 protein, in particular and without limitation, compounds having the general structural scaffold of either compound 4 or compound 7.

It can be another object of the present invention to provide a structural scaffold for p53 reactivating compounds in which multiple moieties or functional groups can be readily substituted in order to examine structure-activity relationships between each such moiety or functional group and the DNA binding mechanism of p53.

It can also be an object of the present invention to identify structural or functional moieties of new p53 reactivating compounds or compositions, as recited above, to selectively target specific types of cancer cells over non-cancerous cells.

It can be a related object to provide one or more compositions with a degree of conformational control, as described herein, that interact with mutant p53, having a functional group structure so as to achieve or induce selective p53 binding, thereby inhibiting the growth of cancerous tumors.

It can be another object of the present invention to provide a method of using compounds and/or compositions, of the type consistent with the preceding objectives, to reactivate p53 binding capabilities in order to inhibit or prevent the growth of cancer cells.

It can be a related object of the present invention to provide a method for characterizing the structure-activity relationship of compounds comprising a structural scaffold, as described herein, in order to design anticancer therapies that selectively target and treat a specific type of cancer.

Other objects, features, benefits and advantages of the present invention will be apparent from this summary and its descriptions of various preferred embodiments, and will be readily apparent to those skilled in the art having knowledge of mutant p53 and p53 reactivation. Such objects, features, benefits and advantages will be apparent from the above as taken in conjunction with the accompanying examples, data, figures and all reasonable inferences to be drawn therefrom.

Accordingly, the present invention relates to a new class of compounds readily synthesized via conventional methods and believed to function via reactivation of mutant p53 protein. The core organic structure of the newly developed compounds allows for facile introduction of different functional groups so that structure-activity relationships for reactivation of mutant p53 can be readily prepared and rapidly explored. Furthermore, the approach is quite versatile, allowing creation of compounds to target different forms of mutant p53 or access to compounds specifically designed to probe the mechanism of p53 reactivation.

In part, the present invention can comprise one or more compounds of a formula

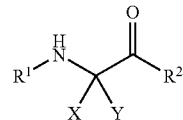

and salts thereof. In such compounds, $R^1$ is H; $R^2$ is selected from phenyl and substituted phenyl moieties; X is selected from H, hydroxymethyl and acetoxymethyl; and Y is acetoxymethyl. In certain embodiments thereof, $R^2$ is phenyl. In certain other embodiments, such a phenyl moiety can be halo-substituted. Without limitation, as illustrated below, a fluoro-substituted phenyl moiety can be incorporated into one or more of such compounds. Likewise, the compounds of this invention can incorporate various other halo-substituent(s), as would be understood by those skilled in the art made aware of this invention. Regardless, where X is H, such a compound can be selected from the (R)-enantiomer, the (S)-enantiomer and a racemic mixture thereof. Salts of such compounds can include those as would be understood by those skilled in the art made aware of this invention. Without limitation, in particular, ammonium salts can comprise the conjugate base of a protic acid.

In various other embodiments, this invention can comprise one or more compounds of a formula

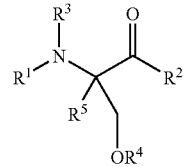

and salts thereof, wherein $R^1$ and $R^3$ can be independently selected from H, alkyl and substituted alkyl, including cyclic alkyl and substituted cyclic alkyl, aromatic, substituted aromatic, acyl and substituted acyl moieties; $R^2$ can be selected from alkyl and substituted alkyl, including cyclic alkyl and substituted cyclic alkyl, alkoxy, substituted alkoxy, aromatic, substituted aromatic, heterocyclic, substituted heterocyclic, acyl and substituted acyl moieties; $R^4$ can be selected from H, alkyl and substituted alkyl, including cyclic alkyl and substituted cyclic alkyl, acyl and substituted acyl moieties; and $R^5$ can be selected from H, alkyl and substituted alkyl, including cyclic alkyl and substituted cyclic alkyl, alkoxy and substituted alkoxy and $CH_2OR^4$. In certain embodiments thereof, $R^2$ can be phenyl or substituted phenyl, such substitutions including but limited to one or more alkyl, substituted alkyl and/or halogen moieties. Without limitation, one or more embodiments can comprise a fluoro-substituted phenyl moiety. Likewise, other such $R^2$ moieties can comprise one or more of the aforementioned substituents. In certain other embodiments, without regard to substitution, $R^2$ can comprise an acyl moiety, such moieties including but not limited to acetyl, propanecarbonyl and benzenecarbonyl moieties. Likewise, without regard to identity of $R^2$, $R^4$ can comprise an acyl moiety. Independently, in addition to those embodiments mentioned above, $R^5$ can likewise comprise such an acyl moiety.

Without restriction to the preceding compounds, the present invention can also comprise a method of using a ketoamine structural component to examine a structural activity relationship. Such a method comprises (1) providing a compound of a formula

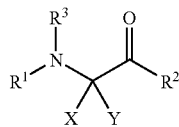

and salts thereof, wherein $R^1$ and $R^3$ can be independently selected from H, alkyl and substituted alkyl, including cyclic alkyl and substituted cyclic alkyl, aromatic, substituted aromatic, acyl and substituted acyl moieties; $R^2$ can be selected from alkyl and substituted alkyl, including cyclic alkyl and substituted cyclic alkyl, alkoxy, substituted alkoxy, aromatic, substituted aromatic, heterocyclic, substituted heterocyclic, acyl and substituted acyl moieties; X and Y can be independently selected from H, alkyl, substituted alkyl, acyl and substituted acyl moieties; (2) contacting such a compound with cells expressing a mutant p53 protein; and (3) determining activity of such a compound against such cells. Moieties $R^1$-$R^3$, X and Y include those discussed above. Chosen or selective change of at least one such moiety can be made to determine affect of such a change on the activity of such a compound.

In further embodiments, the present invention can comprise a method of inhibiting growth of cells expressing a mutant p53 protein. Such a method comprises (1) providing cells expressing a mutant p53 protein; and contacting said cells with a compound of a formula

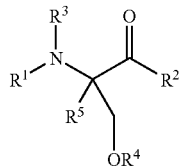

and salts thereof, wherein moieties $R^1$-$R^5$ include those discussed above in conjunction with such a compound. In alternate embodiments, the present invention can comprise a method of using a phenylketone compound to selectively inhibit growth of cells expressing a mutant p53 protein. Such a method comprises (1) providing a phenylketone compound of a formula

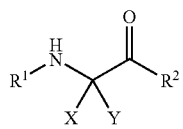

and salts thereof, wherein moieties $R^1$, $R^2$, X and Y include those discussed above; and (2) contacting such a compound with cells expressing a mutant p53 protein.

Figure 2:
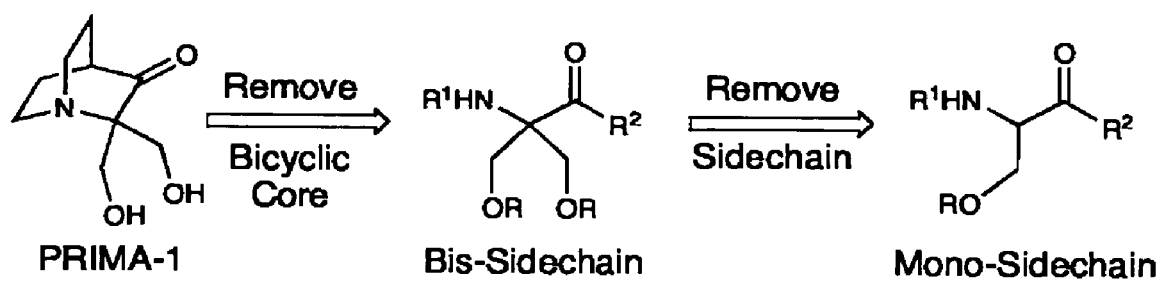
FIG. 2 shows a schematic dissection of the prior art compound PRIMA-1 and, in accordance with this invention but without limitation, an approach to new simplified scaffolds for the present compounds.

For purposes of illustration, compounds of the present invention can include but are not necessarily limited to those available from a scaffold affording a spatial arrangement functionally comparable to but without the structural and chemical impediments of PRIMA-1. A schematic structural evolution is illustrated in FIG. 2. Such a scaffold is not limited by the bicyclic core of PRIMA-1 and thus, provides more flexibility in compound design and synthesis.

Figure 3:
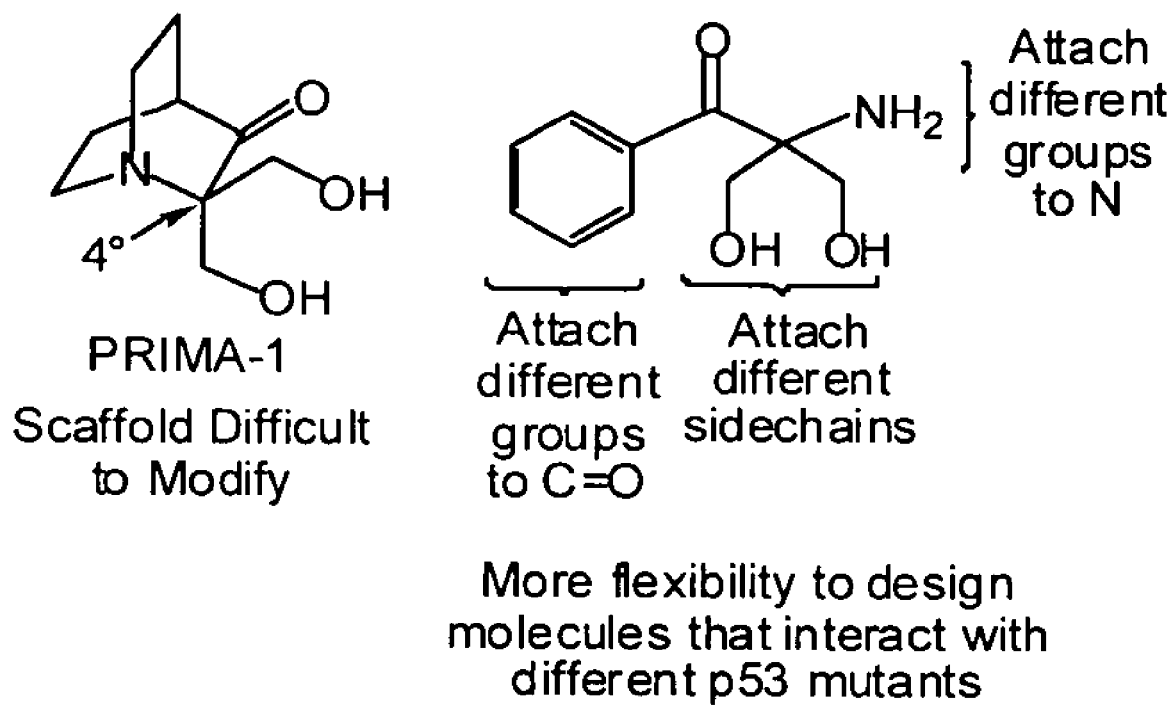
FIG. 3 shows prior art PRIMA-1 and, without limitation, a representative molecular scaffold, in accordance herewith, on which can be based multiple analogs.
Figure 4:
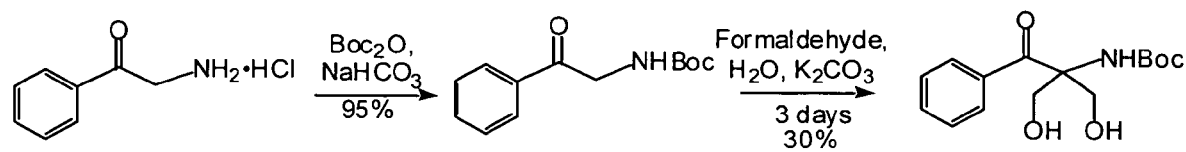
FIGS. 4-5 show, in accordance with the present invention, synthesis of dihydroxy compounds 1 (Boc-protected) and 3 (unprotected acid salt) and the diacetyl hydrochloride, compound 4.
Figure 5:
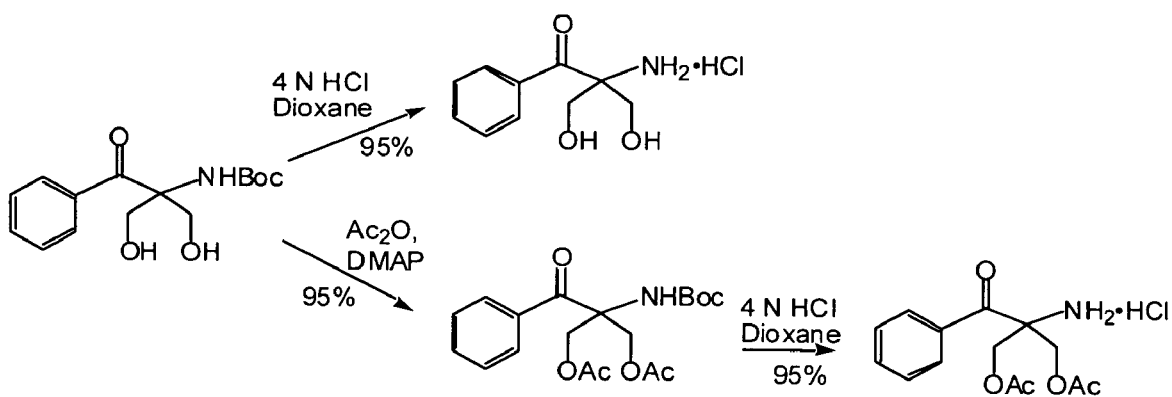

FIG. 2 illustrates an approach to the development of certain compositional aspects of this invention, from PRIMA-1. FIG. 3 shows, by way of compound 4, the design flexibility available with this invention as compared to the prior art (e.g., PRIMA-1). Several such compounds, as illustrated in FIGS. 4-5, can be prepared from 2-aminoacetophenone, with Boc protection, followed by side chain introduction using one or two equivalents of formaldehyde in the presence of base. Boc removal optionally with acetylation, gives desired amines and/or the corresponding acid salts. It will be readily appreciated by those skilled in the art that starting materials, other than 2-aminoacetophenone, including other ketones or substituted ketones providing a comparable chemical structure, scaffold and/or spatial orientation can be used.

Likewise, compounds within the bis and mono-sidechain series were prepared with varying functionality at the amino, hydroxyl, and carbonyl positions. Initially, compounds were prepared starting from 2-aminoacetophenone hydrochloride, and all molecules with one sidechain were racemic (Table 1, 1-7, 10-12).

TABLE 1

Activity on Cells Expressing Mutant p53

| Product[a] | $R^1$ | X | Y | $R^2$ | Activity[b] | Mutant[b] |
|---|---|---|---|---|---|---|
| 1 | Boc | CH$_2$OH | CH$_2$OH | Ph | NA | 281 |
| 2 | Boc | CH$_2$OAc | CH$_2$OAc | Ph | NA | 281 |
| 3 | H | CH$_2$OH | CH$_2$OH | Ph | NA | 281 |
| 4 | H | CH$_2$OAc | CH$_2$OAc | Ph | 10 μM | 281 |
| 5 | H | H | H | Ph | NA | 281 |
| 6 | H | H | CH$_2$OH | Ph | NA | 281 |
| 7 | H | H | CH$_2$OAc | Ph | 5 μM | 175, 281 |
| 8 | H | H | CH$_2$OAc | Ph | 1 μM[c] | 175, 281 |
| 9 | H | H | CH$_2$OAc | Ph | 5 μM[d] | 175 |
| 10 | Ac | H | H | Ph | NA | 175, 281 |
| 11 | Ac | H | CH$_2$OH | Ph | NA | 175, 281 |
| 12 | Ac | H | CH$_2$OAc | Ph | NA | 175, 281 |
| 13 | H | H | CH$_2$OAc | Et | NA | 175, 281 |
| 14 | H | H | CH$_2$OAc | OMe | NA | 281 |
| 15 | H | H | CH$_2$OAc | Morph. | NA | 281 |
| 16 | Me | H | CH$_2$OAc | Ph | NA[e] | 175, 281 |
| 17 | H | Me | CH$_2$OAc | Ph | NA | 175, 281 |

[a]All compounds are (+, −)-mixtures unless otherwise noted; Entries 3–9 and 13–17 were isolated as HCl salts.
[b]PRIMA-1 is active at 25 μM. See examples for cellular assay details; NA = not active under conditions and protocols employed.
[c](S)-enantiomer.
[d](R)-enantiomer.
[e]Compound was found to be in 86% ee as the (S)-enantiomer.

Cellular growth studies were performed on Saos-2 cells, derived from a human osteosarcoma cancer cell line, according to the method described in Example 44. The cells had either no p53 (null) or mutant (mt) p53 at residues 175 and/or 281 (R175H and R281G, respectively). Selective arrest of mutant cells indicates good anticancer activity.

Figure 6A:
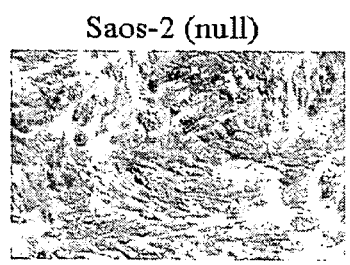
FIGS. 6A-B depict cellular studies on Saos cells comparing the effects of PRIMA-1 to compounds 4 and 7, respectively, illustrating activity at lower concentrations, as compared to PRIMA-1.
Figure 6A:
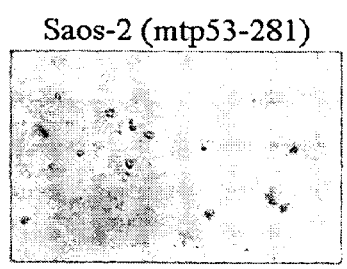
Figure 6A:
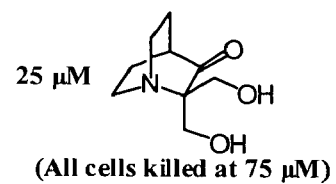
Figure 6A:
Figure 6A:
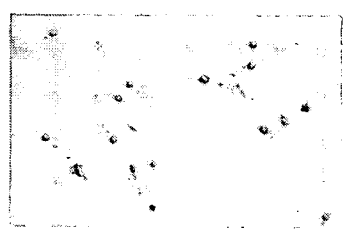
Figure 6A:
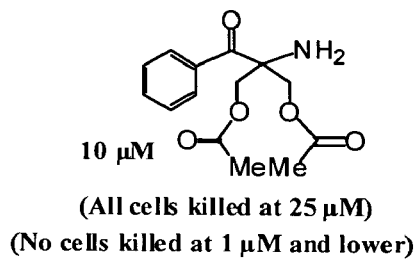
Figure 6B:
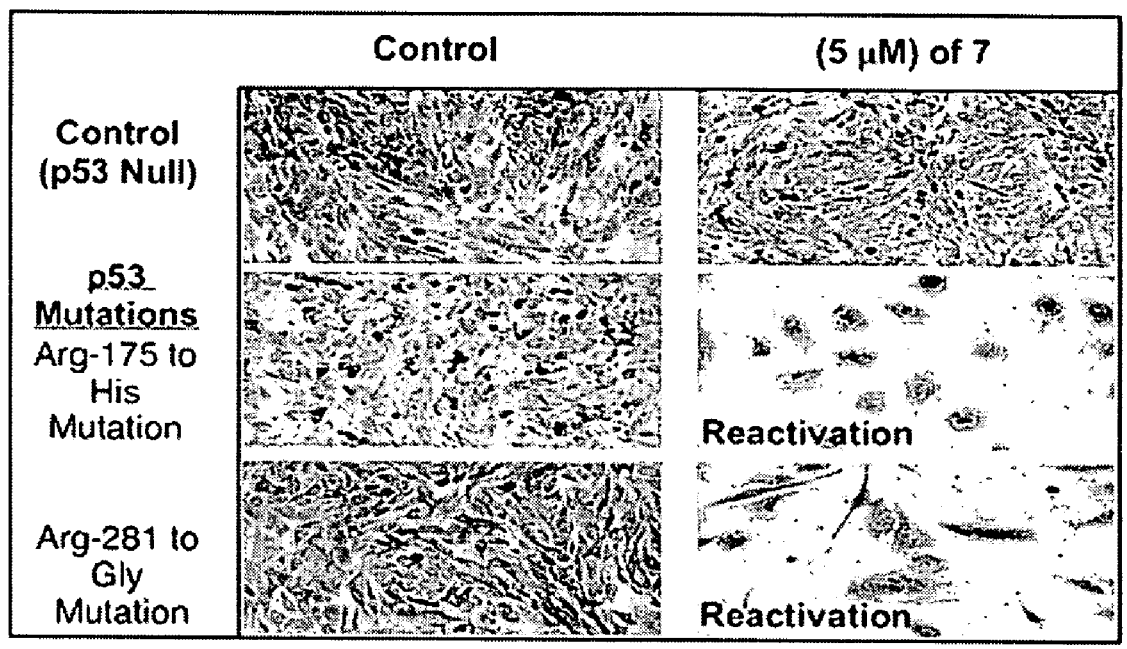

Compound 7 was particularly effective at selectively killing cells expressing R175H and R281G p53 mutants at lower concentrations than PRIMA-1 (racemic 7, FIG. 6B). Compound 4 also showed selectivity for R281G mutants (FIG. 6A). It should be noted that PRIMA-1 is also toxic to p53-null cells at slightly higher concentrations (75 μM), an observation applicable to the design of derivatives more potent and less toxic for therapeutic applications.

These findings are notable, in that the complex PRIMA-1 scaffold can be simplified to the structures of compounds 4 and 7 with the overall activity retained; and that compounds with acetate groups show activity while PRIMA-1 functions without acetate substitution. The present invention is not limited to any particular mechanism of action, and an understanding of any such mechanism is not necessary to practice this invention. However, it is contemplated that these results indicate that compounds 4 and 7 could have an alternative mechanism of action than PRIMA-1, implying that there might be several pathways for reactivating mutant p53, pathways which can be taken using the compounds of this invention.

The positive results obtained with racemic 7 underlined the need to produce both enantiomers of 7 (8 and 9). Therefore, an asymmetric synthesis was developed to produce enantiomerically pure material.

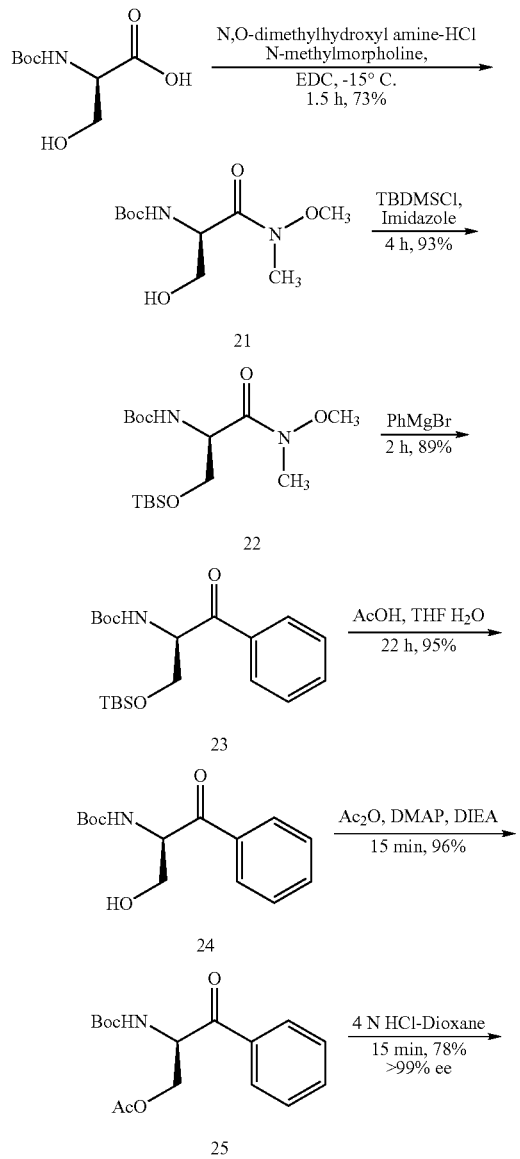

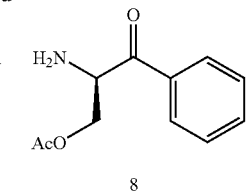

8

Starting from serine (commercially available as either enantiomer), a synthesis of both enantiomers of 7 was developed (Scheme 1). The first step toward (S)-7 (i.e. molecule 8) converted N-Boc-D-serine to Weinreb amide 21. Hydroxyl group protection afforded 22, which was followed by reaction with phenylmagnesium bromide to give 23. Removal of the silyl protecting group using acetic acid was essential for producing 24 without racemization at the α-stereocenter. Finally, acetylation and tert-butyl carbamate deprotection afforded 8 as a single enantiomer. Interestingly, (S)-7 showed improved activity over (±)-7, indicating that chirality plays a role in the observed activity; however, (R)-7 had comparable activity to (±)-7 (Table 1, entries 7-9).

The syntheses developed can be readily modified to afford numerous other analogs of 7. (See, e.g., FIG. 7.) With regard to Scheme 1, and further illustrated in FIG. 7, synthetic intermediate 22 is an entry point to a large number of analogs that possess different functional groups attached to the carbonyl, oxygen, or nitrogen centers. Using such synthetic routes, compounds 11 to 17 were prepared (in racemic form) to gain some insight into SAR for this series of molecules (Table 1). With reference to non-limiting FIG. 7, each of $R^1$-$R^4$ can be independently varied, as described above, by choice of reagent and reaction condition.

While molecules 11 to 17 were not selective in arrest of growth of cells expressing mutant p53 under the conditions employed, the results of these studies can suggest, in certain embodiments the use of a carbonyl as a feature for targeting cells with mutant p53. If the phenyl ketone of 7 is changed to a methyl ester (14), morpholine amide (15), or even an ethyl ketone (16), the desired activity is lost. Therefore, it is shown that ketone structure and electronics can be employed for selective targeting of cells with mutant p53. Furthermore, attaching a methyl group to the nitrogen of 7 (molecule 16) or a methyl group to the α-carbon of 7 (molecule 17) eliminates the desired activity.

Upon identification of those compounds, developing new compounds and/or compositions that reactivate mutant p53 in cellular studies and details of this mechanism in vitro (outside the cell) can be examined. For instance, a determination of whether the new molecules directly refold p53 using conformation specific antibodies can be made. Similar studies with PRIMA-1 have demonstrated that this molecule does indeed refold mutant p53 into a native conformation. However, due to the synthetic limitations of PRIMA-1, it is not possible to probe many properties of this interesting binding interaction. In contrast, with the present invention, a wide variety of different functional groups and substituents are introduced in order to determine the nature of the interactions between p53 and the new compounds. By analyzing a series of different compounds for their ability to refold p53, the most appropriate size, shape, and accessible functional groups of the ideal target molecule can be determined. Such studies will reveal important information about the three-dimensional size and shape of the binding site that leads to refolding of p53. Furthermore, the synthetic strategy of the present invention allows incorporation of photoaffinity labels (such as azide) into these molecules so that specific sites of interaction between these new molecules and p53 can be determined.

Clearly, the reactivation of mutant p53 holds great potential for development of novel anticancer therapies that selectively target tumors, a potential which can be realized through use of compounds and/or methods of this invention. As shown above, several compounds have been identified by selectively arrest growth of cells expressing mutant p53 protein. This initial SAR data should prove useful for elucidation of a mechanism of p53 reactivation by small organic molecules. Importantly, these compounds permit rapid exploration of many different analogs of the newly synthesized molecules and incorporates functional group optimization and selectivity of the molecules of the present invention to identify the optimal target structures for mutated p53. Compared to the prior art, synthetic routes associated with the present class of compounds allow facile variation of molecular components and ready accumulation of corresponding SAR data. Such results will enhance the understanding of mutant p53 reactivation, validate mutant p53 as a therapeutic target, contribute to the general understanding of how organic molecules restore normal protein function, and ultimately may impact new development of therapies for a range of cancer disease states.

EXAMPLES OF THE INVENTION

The following non-limiting examples and data illustrate various aspects and features relating to the compositions and/or related methods of the present invention, including synthesis of compounds 1-6 and/or any of the compounds described above, as are available through the synthetic methodologies described herein. In comparison with the prior art, the present compositions and related methods provide results and data which are surprising, unexpected, and contrary to the prior art. While the utility of this invention is illustrated through the use of several compositions and methods which can be used therewith, it will be understood by those skilled in the art that comparable results are obtainable with various other compositions and/or their methods of use, as are commensurate with the scope of this invention. (Several compounds and/or intermediates are schematically identified with reference to a serine core structure ($H_2NCH_2(O)C$), whether or not prepared from serine.)

General Methods. All reactions were performed in oven dry glassware under a positive pressure of nitrogen unless otherwise noted. Tetrahydrofuran (THF) was distilled from sodium and benzophenone prior to use. Methylene chloride ($CH_2Cl_2$) was distilled from calcium hydride prior to use. Dimethylformamide (DMF) was purified by passage through a bed of activated alumina.[1] Melting points (mp) were obtained on a Thomas Hoover Capillary Melting Point Apparatus and are uncorrected. Optical rotations ($[\alpha]_D$) were measured on a Perkin-Elmer 241 Polarimeter using sodium light (D line, 589.3 nm) and are reported in degrees; concentrations (c) are reported in g/100 mL. Infrared spectra (IR) were obtained on a Bio-Rad FTS-40 FTIR spectrophotometer. Infrared spectra for liquid products were obtained as a thin film on a KBr disk, and spectra for solid products were collected by preparing a KBr pellet containing the title compound. Proton nuclear magnetic resonances ($^1$H NMR) were recorded in deuterated solvents on a Mercury 400 (400 MHz) or a Varian Inova 500 (500 MHz) spectrometers. Chemical shifts are reported in parts per million (ppm, δ) relative to tetramethylsilane (δ0.00). If tetramethylsilane was not present in the deuterated solvent, the residual protio solvent is referenced ($CDCl_3$, δ 7.27; $D_2O$, δ 4.80; DMSO-$d_6$, δ 2.50). $^1$H NMR splitting patterns are designated as singlet (s), doublet (d), triplet (t), quartet (q), or septet (sep). Splitting patterns that could not be interpreted or easily visualized are designated as multiplet (m) or broad (br). Coupling constants are reported in Hertz (Hz). Proton-decoupled ($^{13}$C-NMR) spectra were recorded on a Mercury 400 (100 MHz) or a Varian Inova 500 (125 MHz) spectrometer and are reported in ppm using the solvent as an internal standard ($CDCl_3$, δ 77.23; DMSO, δ 39.52). Electrospray mass spectra (ESI-MS) were obtained using a Micromass Quattro II Triple Quadrupole HPLC/MS/MS Mass Spectrometer. Elemental Analysis data were collected by Atlantic Microlab, Inc. High performance liquid chromatography (HPLC) chiral analysis was conducted on a Varian Workstation using a (S,S) WHELK-O Column eluting with a solvent system of 9:1 Hexanes:IPA at 1.5 mL/min. Boc-N-methyl-L-serine was purchased from Chem-Impex International, Inc. All amino acid starting materials, $Boc_2O$, and EDC were purchased from Advanced ChemTech and used without further purification. Unless otherwise noted, all other commercially available reagents and solvents were purchased from Aldrich and used without further purification.

Abbreviations: ($Ac_2O$), acetic anhydride; ($Boc_2O$), di-tert-butyl diacarbonate; (DIEA), N,Ndiisopropylethylamine; (DMAP), 4-(dimethylamino)pyridine; (EDC), 1-ethyl-3-(3-dimethylaminopropyl)-carbodimide; (HOBt), 1-hydroxy-benztriazole; (TEA), triethylamine. (TBDMSCl), tert-butyldimethylsilyl chloride.

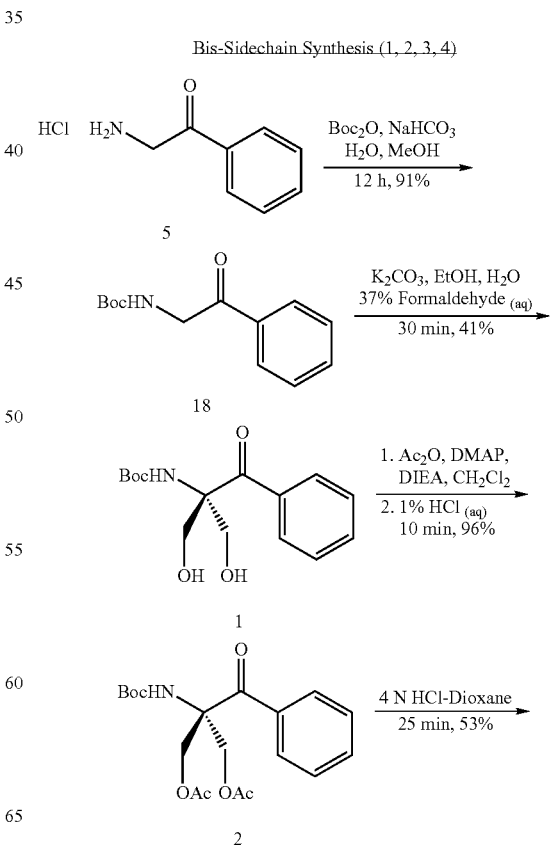

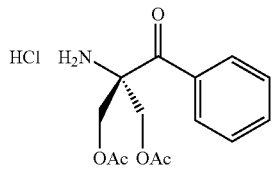

4

Example 1

Tert-butyl 1-oxo-1-phenylethan-2-ylcarbamate (18): 2-oxo-2-phenylethanaminium chloride (5) (5.0 g, 29.0 mmol, 1.0 equiv.) was added to a 250 mL RBF followed by $dH_2O$ (100 mL). Next, $NaHCO_3$ (6.1 g, 72.5 mmol, 2.5 equiv.), MeOH (100 mL), and $Boc_2O$ (9.5 g, 43.5 mmol, 1.5 equiv.) were added to the reaction flask. The reaction was stirred vigorously overnight for 20 h. A white precipitate formed while stirring. The reaction mixture was transferred to a 1 L Erlenmeyer flask containing ice cold $H_2O$ (400 mL) and the mixture was filtered with a Buchner funnel. The resulting solid was washed with $dH_2O$ (150 mL) and dried under vacuum to give 6.2 g (91%) of 18 as a white fluffy solid. $R_f$=0.64 (2% $MeOH/CH_2Cl_2$); mp=63-65° C.; IR (KBr) 3354, 2976, 2930, 1718, 1687, 1523, 1365, 1230, 1173 $cm^{-1}$; $^1H$ NMR (500 MHz, $CDCl_3$) δ 7.96 (d, J=7.5 Hz, 2H, Ph-$\underline{H}$), 7.61 (t, J=7.5 Hz, 1H, Ph-$\underline{H}$), 7.49 (t, J=7.5 Hz, 2H, Ph-$\underline{H}$), 5.58 (br s, 1H, carbamate-N$\underline{H}$), 4.67 (d, J=4.0 Hz, 2H, Boc-NH—C$\underline{H}_2$), 1.48 (s, 9H, t-butyl-C$\underline{H}_3$); $^{13}C$ NMR (125 MHz, $CDCl_3$) δ 194.6, 155.9, 134.7, 134.1, 129.0, 128.0, 78.0, 47.7, 28.5; LRMS (ESI-MS m/z): Mass calcd for $C_{13}H_{17}NNaO_3$ [M+Na]$^+$, 258.27. Found 258. Spectroscopic data were consistent with the literature data for this compound.

Example 2

Tert-butyl 3-hydroxy-2-(hydroxymethyl)-1-oxo-1-phenylpropan-2-ylcarbamate (1): tert-butyl 1-oxo-1-phenylethan-2-ylcarbamate (18) (1.4 g, 6.0 mmol, 1.0 equiv.) was added to a 100 mL RBF followed by EtOH (21 mL). Next, a 37% solution of formaldehyde (14.5 mL, 180 mmol, 30.0 equiv.) was added to the reaction mixture and the solution heated to 35° C. Finally, a 3.0 M solution of $K_2CO_3$ (410 mg, 3.0 mmol, 1.0 mL $dH_2O$, 0.5 equiv.) was added to the reaction flask and the solution stirred vigorously for 30 min. The solution was neutralized with 1% HCl, transferred to a separatory funnel with a 2.3 M solution of NaCl (12.0 g, 205 mmol, 90.0 mL $H_2O$), and extracted with $CH_2Cl_2$ (5×60 mL). The organic layers were combined and dried over $Na_2SO_4$. The resulting solution was concentrated on a rotary evaporator and dried under vacuum to give 2.9 g of crude oil. The residue was purified by flash column chromatography (4% $MeOH/CH_2Cl_2$) to give 720 mg (41%) of 1 as a white solid. $R_f$=0.20 (4% $MeOH/CH_2Cl_2$); mp=127-130° C.; IR (KBr) 3437, 3372, 2980, 2967, 1701, 1671, 1504, 1282, 1026 $cm^{-1}$; $^1H$ NMR (500 MHz, $CDCl_3$) δ Major Rotamer: 8.03 (m, 2H, Ph-$\underline{H}$), 7.43 (br s, 3H, Ph-$\underline{H}$), 5.87 (br s, 1H, carbamate-N$\underline{H}$), 5.35 (br s, 1H, Boc-NH—C$\underline{H}$), 4.25 (d, J=11.0 Hz, 2H, CH—C$\underline{H}_2$), 4.02 (d, J=11.0 Hz, 2H, CH—C$\underline{H}_2$), 3.31 (br s, 2H, (C$\underline{H}_2$—O$\underline{H}_2$), 1.28 (s, 9H, t-butyl-C$\underline{H}_3$). Minor Rotamer: 8.19 (br s, 2H, Ph-$\underline{H}$), 7.52 (br s, 3H, Ph-$\underline{H}$), 1.07 (s, 9H, t-butyl-C$\underline{H}_3$); $^{13}C$ NMR (125 MHz, $CDCl_3$) δ 202.2, 201.1, 155.4, 154.9, 136.3, 135.1, 133.4, 132.7, 129.1, 128.7, 128.4, 82.2, 80.7, 68.2, 67.4, 64.6, 64.2, 28.2, 27.7; LRMS (ESI-MS m/z): Mass calcd for $C_{15}H_{21}NO_5$ [M]$^+$, 295.33. Found 296. Anal. calcd for $C_{15}H_{21}NO_5$: C, 61.00; H, 7.17; N, 4.74 Found: C, 60.90; H, 7.17; N, 4.74.

Example 3

Tert-butyl 3-acetoxy-2-(acetoxymethyl)-1-oxo-1-phenylpropan-2-ylcarbamate (2): tert-butyl 3-hydroxy-2-(hydroxymethyl)-1-oxo-1-phenylpropan-2-ylcarbamate (1) (440 mg, 1.5 mmol, 1.0 equiv.) was added to a 100 mL RBF followed by $CH_2Cl_2$ (15 mL). The resulting solution was cooled to 0° C. via an ice bath. Next, acetic anhydride (340 μL, 3.6 mmol, 2.4 equiv.), DIEA (630 μL, 3.6 mmol, 2.4 equiv.), and DMAP (36 mg, 0.3 mmol, 0.2 equiv.) were added to the reaction flask. The reaction solution stirred for 30 min at 0° C., was quenched with 1% HCl (25 mL), and transferred to a separatory funnel with $CH_2Cl_2$ (75 mL). The resulting organic layer was washed with 1% HCl (2×25 mL) and sat. NaCl (2×25 mL). The organic layers were dried over $Na_2SO_4$, concentrated on a rotary evaporator, and dried under vacuum to give 550 mg (96%) of 2 as a clear oil which crystallized to a white solid upon standing. $R_f$=0.73 (100% EtOAc); mp=112-113° C.; IR (KBr) 3331, 2982, 1745, 1697, 1674, 1523, 1253, 1214, 1053 $cm^{-1}$; 1H NMR (500 MHz, $CDCl_3$) δ Major Rotamer: 7.97 (m, 2H, Ph-$\underline{H}$), 7.43 (m, 3H, Ph-$\underline{H}$), 5.51 (br s, 1H, carbamate-N$\underline{H}$), 4.59 (d, J=11.0 Hz, 4H, CH—C$\underline{H}_2$), 2.07 (s, 6H, (O═C—C$\underline{H}_3$)$_2$), 1.30 (s, 9H, t-butyl-C$H_3$). Minor Rotamer: 8.29 (br s, 2H, Ph-$\underline{H}$), 7.52 (br s, 3H, Ph-$\underline{H}$), 5.19 (br s, 1H, carbamate-N$\underline{H}$), 4.71 (d, J=11.0 Hz, 4H, CH—C$\underline{H}_2$), 1.10 (s, 9H, t-butyl-C$\underline{H}_3$); $^{13}C$ NMR (125 MHz, $CDCl_3$) δ 197.3, 196.7, 170.4, 154.1, 136.0, 135.3, 133.1, 132.5, 128.9, (128.3)$_2$, 82.5, 80.8, 65.3, 64.0, 63.7, 28.2, 27.6, 20.9; LRMS (ESI-MS m/z): Mass calcd for $C_{19}H_{25}NNaO_7$ [M+Na]$^+$, 402.39. Found 402. Anal. calcd for $C_{19}H_{25}NO_7$: C, 60.15; H, 6.64; N, 3.69 Found: C, 60.16; H, 6.84; N, 3.73.

Example 4

3-Acetoxy-2-(acetoxymethyl)-1-oxo-1-phenylpropan-2-aminium chloride (4): tert-butyl 3-acetoxy-2-(acetoxymethyl)-1-oxo-1-phenylpropan-2-ylcarbamate (2) (420 mg, 1.1 mmol, 1.0 equiv.) was added to a 100 mL RBF and a 4.0 N HCl-Dioxane solution (8.3 mL, 33.0 mmol, 30.0 equiv) was added. The solution was stirred for 25 min and the solvent was evaporated with a steady stream of $N_{2\ (g)}$. The resulting residue was taken up in Et2O (40 mL) giving a sticky solid. The mixture was cooled by partial evaporation and the solid was triturated and stirred for 10 min. The precipitate was filtered, washed with Et$_2$O (2×50 mL), and dried under vacuum to give 180 mg (53%) of 4 as a white solid. mp=122-123° C.; $^1H$ NMR (500 MHz, DMSO) δ 9.01 (br s, 3H, C—N$\underline{H}_3$), 7.97 (d, J=7.0 Hz, 2H, Ph-$\underline{H}$), 7.72 (t, J=7.5 Hz, 1H, Ph-$\underline{H}$), 7.58 (t, J=7.5 Hz, 2H, Ph-$\underline{H}$), 4.78 (A$\underline{B}$, J=12.5 Hz, 2H, CC$\underline{H}_2$), 4.66 (A$\underline{B}$, J=12.5 Hz, 2H, C—C$\underline{H}_2$), 1.97 (s, 6H, (O═C—C$\underline{H}_3$)$_2$); $^{13}C$ NMR (125 MHz, DMSO) δ 193.8, 169.4, 133.7, 133.6, 129.0, 128.2, 67.2, 62.8, 20.4; LRMS (ESI-MS m/z): Mass calcd for $C_{14}H_{18}NO_5$ [M]$^+$, 280.30. Found 280.

Bis-Sidechain Synthesis (3)

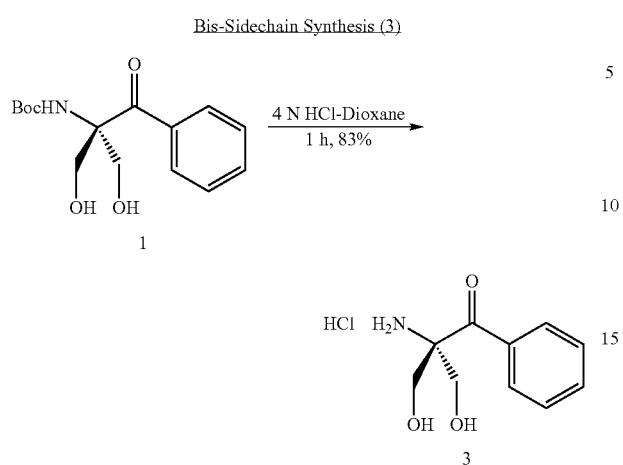

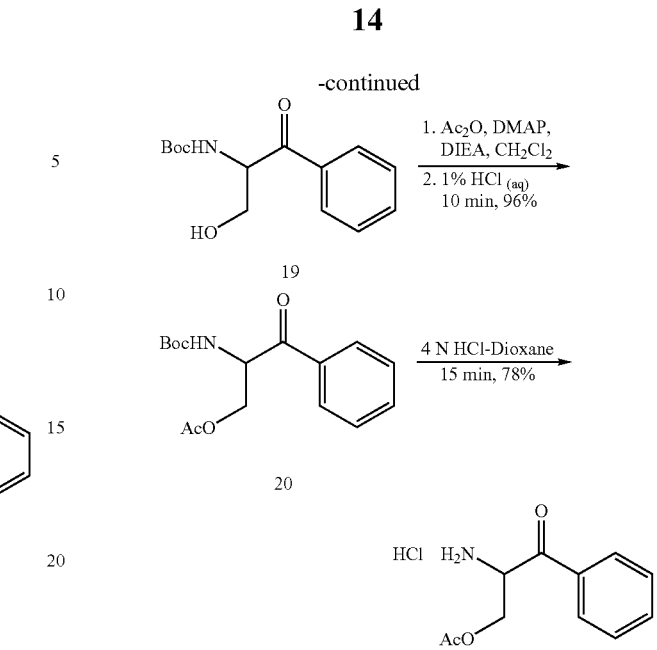

Example 5

3-Hydroxy-2-(hydroxymethyl)-1-oxo-1-phenylpropan-2-aminium chloride (3): tert-butyl 3-hydroxy-2-(hydroxymethyl)-1-oxo-1-phenylpropan-2-ylcarbamate (1) (120 mg, 0.4 mmol, 1.0 equiv.) was added to a 10 mL RBF followed by a 4.0 N HCl-Dioxane solution (3.0 mL, 12.0 mmol, 30.0 equiv.). The solution was stirred for 1 h and 2 mL of the solvent was evaporated with a steady stream of $N_{2\,(g)}$. The resulting suspension was taken up in $Et_2O$ giving a white precipitate. The mixture was filtered, washed with $Et_2O$ (3×10 mL) and dried under vacuum to give 77 mg (83%) of 3 as a white solid. Decomposition occurs at 173-174° C.; $^1H$ NMR (500 MHz, DMSO) δ 8.51 (br s, 3H, C—N$\underline{H}_3$), 7.89 (d, J=7.5 Hz, 2H, Ph-$\underline{H}$), 7.64 (t, J=7.5 Hz, 1H Ph-$\underline{H}$), 7.53 (t, J=7.5 Hz, 2H, Ph-$\underline{H}$), 5.77 (s, 2H, (CH$_2$—O$\underline{H}$)$_2$), 4.11 (d, J=12.0 Hz, 2H, C—C$\underline{H}_2$), 3.89 (d, J=12.0 Hz, 2H, C—C$\underline{H}_2$); $^{13}C$ NMR (125 MHz, DMSO) δ 197.6, 135.1, 132.7, 128.7, 128.1, 73.1, 61.2; LRMS (ESI-MS m/z): Mass calcd for $C_{10}H_{14}NO_3$ [M]$^+$, 296.22. Found 296. Anal. calcd for $C_{10}H_{14}ClNO_3$: C, 51.84; H, 6.33; N, 6.05 Found: C, 51.70; H, 6.33; N, 5.84.

Racemic Synthesis: Mono-Substituted (5, 7)

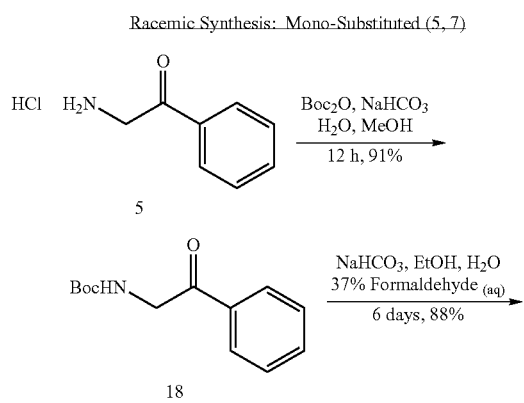

Example 6

Tert-butyl 3-hydroxy-1-oxo-1-phenylpropan-2-ylcarbamate (19): tert-butyl 1-oxo-1-phenylethan-2-ylcarbamate (18) (2.4 g, 10.0 mmol, 1.0 equiv.) was added to a 100 mL RBF followed by EtOH (41 mL, 200 proof). Next, a 0.5 M solution of NaHCO$_3$ (420 mg, 5.0 mmol, 0.5 equiv.) was added followed by a 37% solution of formaldehyde (1.2 mL, 15.0 mmol, 1.5 equiv.). The solution was stirred at rt. for 6 days and transferred to a separatory funnel with a 1.0 M solution of NaCl (5.0 g, 85.5 mmol). The solution was extracted with CH$_2$Cl$_2$ (5×50 mL). The organic layer was dried over Na$_2$SO$_4$, concentrated on a rotary evaporator, and dried under vacuum to give a crude light yellow oil. The residue was purified by flash column chromatography (30% EtOAc/hexanes) to give 2.3 g (88%) of 19 as a colorless oil which crystallized to a white solid. (Note: It is essential to use a 100 mL RBF for full vortex stirring over the entire reaction period) $R_f$=0.16 (30% EtOAc/Hexanes); mp=69-71° C.; IR (film) 3420, 2976, 2931, 1683, 1503, 1366, 1165, 1061 cm$^{-1}$; $^1H$ NMR (500 MHz, CDCl$_3$) δ 8.00 (d, J=7.0 Hz, 2H, Ph-$\underline{H}$), 7.60 (t, J=7.0 Hz, 1H, Ph-$\underline{H}$), 7.48 (t, J=7.0 Hz, 2H, Ph-$\underline{H}$), 5.96 (d, J=6.0 Hz, 1H, carbamate-N$\underline{H}$), 5.36 (br s, 1H, Boc-NH—C$\underline{H}$), 4.00 (m, 1H, CH—C$\underline{H}_2$), 3.86 (m, 1H, CH—C$\underline{H}_2$), 3.29 (br s, 1H, CH$_2$—O$\underline{H}$), 1.45 (s, 9H, t-butyl-C$\underline{H}_3$); $^{13}C$ (125 MHz, CDCl$_3$) δ 197.4, 156.3, 134.6, 134.1, 129.0, 128.9, 80.5, 64.7, 58.1, 28.4; LRMS (ESI-MS m/z): Mass calcd for $C_{14}H_{19}NNaO_4$ [M+Na]$^+$, 288.29. Found 288. Anal. calcd for $C_{14}H_{19}NO_4$: C, 63.38; H, 7.22; N, 5.28 Found: C, 63.22; H, 7.25; N, 5.28.

Example 7

2-(Tert-butoxycarbonyl)-3-oxo-3-phenylpropyl acetate (20): tert-butyl 3-hydroxy-1-oxo-1-phenylpropan-2-ylcarbamate (19) (800 mg, 3.0 mmol, 1.0 equiv.) was added to a 100 mL RBF followed by CH$_2$Cl$_2$ (30 mL). The resulting solution was cooled to 0° C. via an ice bath. Next, acetic anhydride (340 μL, 3.6 mmol, 1.2 equiv.), DIEA (630 μL, 3.6 mmol, 1.2 equiv.), and DMAP (36 mg, 0.3 mmol, 0.1 equiv.) were added to the reaction flask. The reaction solution stirred for 15 min at 0° C., was quenched with 1% HCl (50 mL), and transferred to a separatory funnel with CH$_2$Cl$_2$ (100 mL). The resulting organic layer was washed with 1% HCl (2×40 mL) and sat. NaCl (2×40 mL). The organic layer was dried over Na$_2$SO$_4$, concentrated on a rotary evaporator, and dried under vacuum to give 1.2 g of a crude colorless oil. The residue was purified by flash column chromatography (25% EtOAc/hexanes) (Note: Only if purification is necessary) to give 870 mg (96%) of 20 as a colorless oil which crystallized to a white solid upon standing. R$_f$=0.30 (25% EtOAc/hexanes); mp=72-74° C.; IR (film) 3343, 3354, 3062, 2976, 2933, 1745, 1713, 1687, 1506, 1366, 1230, 1164, 1053 cm$^{-1}$; $^1$H NMR (500 MHz, CDCl$_3$) δ 8.02 (d, J=7.5 Hz, 2H, Ph-H), 7.62 (t, J=7.5 Hz, 1H, Ph-H), 7.51 (t, J=7.5 Hz, 2H, Ph-H), 5.66 (d, J=8.0 Hz, 1H, carbamate-NH), 5.59 (m, 1H, Boc-NH—CH), 4.51 (dd, J=11.5, 4.0 Hz, 1H, CH—CH$_2$), 4.18 (dd, J=11.5, 6.0 Hz, 1H, CH—CH$_2$), 1.99 (s, 3H, O═C—CH$_3$), 1.46 (s, 9H, t-butyl-CH$_3$); $^{13}$C NMR (125 MHz, CDCl$_3$) δ 196.2, 170.9, 155.5, 134.6, 134.3, 129.1, 128.8, 80.3, 64.9, 54.6, 28.5, 20.8; LRMS (ESI-MS m/z): Mass calcd for C$_{16}$H$_{21}$NNaO$_5$ [M+Na]$^+$, 330.33. Found 330. Anal. calcd for C$_{16}$H$_{21}$NO$_5$: C, 62.53; H, 6.89; N, 4.56 Found: C, 62.19; H, 6.98; N, 4.48.

Example 8

3-Acetoxy-1-oxo-1-phenylpropan-2-aminium chloride (7): 2 (tertbutoxycarbonyl)-3-oxo-3-phenylpropyl acetate (20) (310 mg, 1.0 mmol, 1.0 equiv.) was added to a 100 mL RBF followed by a 4.0 N HCl-Dioxane solution (7.5 mL, 30.0 mmol, 30.0 equiv.). The solution was stirred for 15 min and a precipitate formed. Et$_2$O (50 mL) was added to the reaction flask and the precipitate was filtered with a Buchner funnel. The precipitate was then washed with an additional portion of Et$_2$O (50 mL) and dried under vacuum to give 190 mg (78%) of 7 as a white solid. Decomposition occurs between 148-151° C.; $^1$H NMR (500 MHz, DMSO) δ 8.94 (s, 3H, CH—NH$_3$$^+$) 8.09 (d, J=7.5 Hz, 2H, Ph-H), 7.73 (t, J=7.5 Hz, 1H, Ph-H), 7.59 (t, J=7.5 Hz, 2H, Ph-H), 5.47 (s, 1H, $^+$NH$_3$—CH), 4.60 (AB, J=12.5 Hz, 1H, CH—CH$_2$), 4.42 (AB, J=12.5 Hz, 1H, CH—CH$_2$) 1.94 (s, 3H, O═C—CH$_3$); $^{13}$C NMR (125 MHz, DMSO) δ 193.3, 169.9, 134.6, 133.3, 129.1, 128.7, 62.0, 54.3, 20.5; LRMS (ESI-MS m/z): Mass calcd for C$_{11}$H$_{14}$NO$_3$ [M+H]$^+$, 208.23. Found 208. Anal. calcd for C$_{11}$H$_{14}$ClNO$_3$: C, 54.22; H, 5.79; N, 5.75 Found: C, 54.13; H, 5.77; N, 5.69.

Racemic Synthesis: Mono-Sidechain (6)

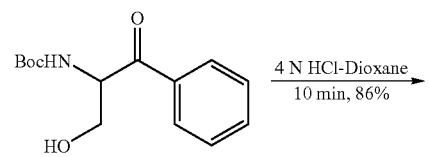

19

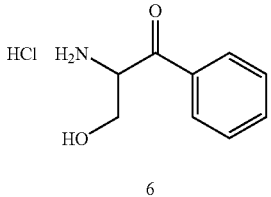

6

Example 9

3-Hydroxy-1-oxo-1-phenylpropan-2-aminium chloride (6): tert-butyl 3-hydroxy-1-oxo-1-phenylpropan-2-ylcarbamate (19) (270 mg, 1.0 mmol, 1.0 equiv) was added to a 25 mL RBF and a 4.0 N HCl-Dioxane solution (7.5 mL, 30.0 mmol, 30.0 equiv.) was added. The solution was stirred at rt. for 25 min, and 5 mL dioxane was evaporated with a steady stream of N$_2$ $_{(g)}$. Next, Et$_2$O (10 mL) was added to the reaction flask and a white precipitate formed. The soln was stirred for 10 min and filtered with a Buchner funnel. The precipitate was dried under vacuum to give 170 mg (86%) of 6 as a white solid. mp=160-162° C.; $^1$H NMR (500 MHz, DMSO) δ 8.94 (s, 3H, CH—NH$_3$) 8.07 (d, J=7.0 Hz, 2H, Ph-H), 7.73 (t, J=7.0 Hz, 1H, Ph-H), 7.59 (t, J=7.5 Hz, 2H, Ph-H), 5.53 (br s, 1H, CH$_2$—OH), 5.19 (s, 1H, $^+$NH$_3$—CH), 3.94 (d, J=11.5 Hz, 1H, CH—CH$_2$), 3.85 (d, J=11.5 Hz, 1H, CH—CH$_2$); $^{13}$C NMR (125 MHz, DMSO) δ 194.5, 134.3, 133.7, 129.1, 128.8, 60.6, 57.6; LRMS (ESI-MS, n/z): Mass calcd for C$_9$H$_{12}$NO$_2$ [M]$^+$, 166.20. Found 166. Anal. calcd for C$_9$H$_{12}$ClNO$_2$: C, 53.61; H, 6.00; N, 6.95 Found: C, 53.26; H, 6.13; N, 6.96.

Enantiomerically Pure Synthesis (8, 9): (D)-Enantiomer

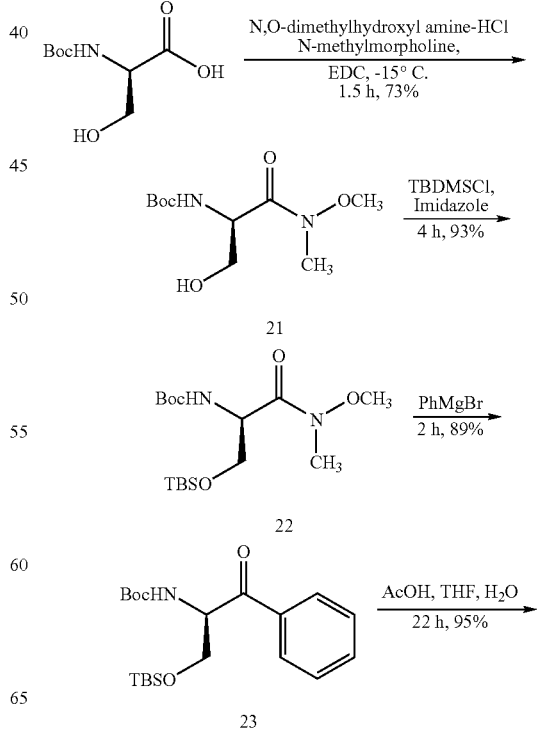

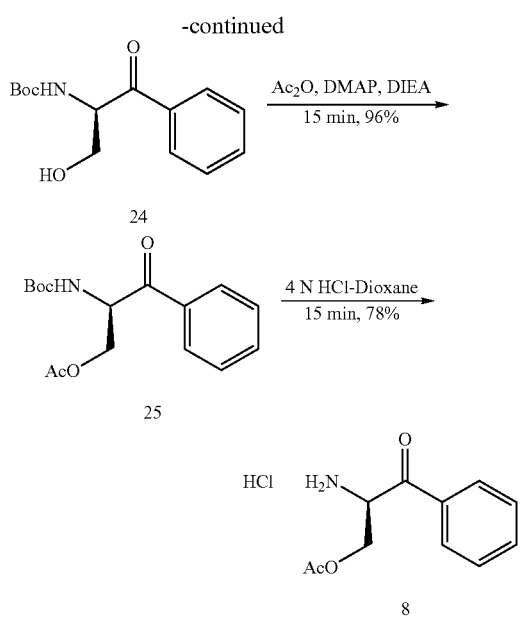

Example 10

(R)-Tert-butyl 3-hydroxy-1-(methoxy(methyl)amino)-1-oxopropan-2-ylcarbamate (21): (R)-2-(tert-butoxycarbonyl)-3-hydroxypropanoic acid (5.0 g, 24.4 mmol, 1.0 equiv.) was added to a 250 mL RBF followed by $CH_2Cl_2$ (90 mL) and cooled to $-15°$ C. via an ice/salt water bath. Next, N,O-dimethylhydroxyl amine-HCl (2.5 g, 25.6 mmol, 1.1 equiv.) and N-methylmorpholine (2.8 mL, 25.6 mmol, 1.1 equiv) were added to the reaction flask. EDC (4.9 g, 25.6 mmol, 1.1 equiv.) was then added to the reaction flask in 5 equal portions over the first 30 min (1 portion per 6 min). After completely charged with EDC, the reaction was allowed to stir an additional 1 h at $-15°$ C. The reaction was quenched with ice cold 1% HCl (25 mL) and transferred to a separatory funnel with $CH_2Cl_2$ (100 mL). The mixture was washed with 1% HCl (3×30 mL), sat. $NaHCO_3$ (2×30 mL), and sat. NaCl (1×30 mL). The organic layer was separated and dried over $Na_2SO_4$. The solution was concentrated on a rotary evaporator and dried under vacuum to give 4.4 g (73%) of 21 as a white solid. $R_f$=0.36 (100% EtOAc); mp=115-116° C.; $[\alpha]_D^{23.5}$=+13.3 (c 1.00, MeOH); IR (KBr) 3470, 3354, 2977, 2943, 1703, 1645, 1538, 1363, 1180, 1078, 1064 $cm^{-1}$; $^1H$ NMR (500 MHz, $CDCl_3$) δ 5.66 (br d, J=6.0 Hz, 1H, carbamate-NH), 4.81 (br s, 1H, Boc-NH—CH), 3.82 (m, 2H, CH—CH$_2$), 3.79 (s, 3H, N—OCH$_3$), 3.24 (s, 3H, N—CH$_3$), 2.86 (br s, 1H, CH$_2$—OH), 1.45 (s, 9H, t-butyl-CH$_3$); $^{13}C$ (125 MHz, $CDCl_3$) δ 171.1, 156.1, 80.2, 63.9, 61.8, 52.6, 32.3, 28.5; LRMS (ESI-MS m/z): Mass calcd for $C_{10}H_{20}N_2O_5$ $[M]^+$, 248.28. Found 249. Spectroscopic data were consistent with the literature data for this compound.

Example 11

(R)-tert-butyl 3-(tert-butyldimethylsilyloxy)-1 (methoxy(methyl)amino)-1-oxopropan-2-ylcarbamate (22): (R)-tert-butyl 3-hydroxy-1-(methoxy(methyl)amino)-1-oxopropan-2-ylcarbamate (21) (4.4 g, 17.5 mmol, 1.0 equiv.) was added to a 100 mL RBF followed by DMF (35 mL) and cooled to 0° C. via an ice bath. Next, TBDMSCl (2.9 g, 19.3 mmol, 1.1 equiv.) and imidazole (2.4 g, 35.1 mmol, 2.0 equiv.) were added to the reaction flask. The solution was stirred at 0° C. for 1 h and then allowed to warm to rt, stirring an additional 2 h. The reaction solution was transferred to a 500 mL separatory funnel with EtOAc (150 mL). The mixture was washed with 1% HCl (3×40 mL), sat. $NaHCO_3$ (1×40 mL), and sat. NaCl (2×40 mL). The organic layer was separated and dried over $Na_2SO_4$. The solution was concentrated on a rotary evaporator and dried under vacuum to give 5.9 g (93%) of 22 as a colorless oil. $R_f$=0.54 (50% EtOAc/hexanes); $[\alpha]_D^{23.5}$=+3.55 (c 1.22, MeOH); IR (film) 3437, 3324, 2953, 2929, 2884, 2856, 1715, 1666, 1496, 1471, 1365, 1253, 1171, 1114 $cm^{-1}$; $^1H$ NMR (500 MHz, $CDCl_3$) δ 5.34 (br d, J=8.5 Hz, 1H, carbamate-NH), 4.73 (br s, 1H, Boc-NH—CH), 3.83 (m, 1H, CH—CH$_2$), 3.77 (m, 1H, CH—CH$_2$), 3.73 (s, 3H, N—OCH$_3$), 3.19 (s, 3H, NCH$_3$), 1.41 (s, 9H, Boc-t-butyl-CH$_3$), 0.84 (s, 9H, Si-t-butyl-CH$_3$), 0.00 (s, 6H, Si—(CH$_3$)$_2$); $^{13}C$ NMR (125 MHz, $CDCl_3$) δ 170.9, 155.5, 79.7, 63.6, 61.6, 52.6, 32.3, 28.5, 25.9, 18.4, −5.4; LRMS (ESI-MS m/z): Mass calcd for $C_{16}H_{34}N_2O_5Si$ $[M]^+$, 362.54. Found 363. Anal. calcd for $C_{16}H_{34}N_2O_5Si$: C, 53.01; H, 9.45; N, 7.73 Found: C, 53.26; H, 9.63; N, 7.68.

Example 12

(R)-tert-butyl 3-(tert-butyldimethylsilyloxy)-1-oxo-1-phenylpropan-2-ylcarbamate (23): (R)-tert-butyl 3-(tert-butyldimethylsilyloxy)-1 (methoxy(methyl)amino)-1-oxopropan-2-ylcarbamate (22) (2.2 g, 6.0 mmol, 1.0 equiv.) was added to a 250 mL RBF followed by THF (60 mL). The mixture was cooled to 0° C. via an ice bath and a 1.0 M solution of PhMgBr in THF (18.0 mL, 18.0 mmol, 3.0 equiv.) was added over 8 min. The reaction stirred for 1.0 h at 0° C. and the ice bath was removed. The reaction stirred for an additional 1.0 h at rt. and was again cooled to 0° C. via an ice bath. Next, the reaction was quenched by addition of 1.0 M HCl (55 mL). The solution was transferred to a separatory funnel with additional 1.0 M HCl (40 mL) and extracted with EtOAc (3×100 mL). The organic layers were washed with sat. NaCl (1×50 mL) and dried over $Na_2SO_4$. The solution was then concentrated on a rotary evaporator and dried under vacuum to give 2.5 g of crude material. The residue was purified by flash column chromatography (10% EtOAc/Hexanes) to give 2.0 g (89%) of 23 as a colorless oil. $R_f$=0.29 (10% EtOAc/Hexanes); $[\alpha]_D^{23.5}$=−12.3 (c 1.26, MeOH); IR (film) 3433, 3360, 3062, 2952, 2929, 2883, 2856, 1715, 1688, 1498, 1253, 1167, 1114 $cm^{-1}$; $^1H$ NMR (500 MHz, $CDCl_3$) δ 7.97 (d, J=7.0 Hz, 2H, Ph-H), 7.61 (t, J=7.0 Hz, 1H, Ph-H), 7.50 (t, J=7.0 Hz, 2H, Ph-H), 5.73 (d, J=7.5 Hz, 1H, carbamate-NH), 5.35 (m, 1H, Boc-NH—CH), 3.97 (dq, J=9.5, 2.5 Hz, 2H, CH—CH$_2$), 1.50 (s, 9H, Boc-t-butyl-CH$_3$), 0.79 (s, 9H, Si-t-butyl-CH$_3$), −0.07 (s, 3H, Si—CH$_3$), −0.12 (s, 3H, Si—CH$_3$); $^{13}C$ (125 MHz, $CDCl_3$) δ 197.9, 155.5, 135.6, 133.5, 128.8, 128.7, 79.9, 64.5, 57.4, 28.5, 25.8, 18.2, −5.6, −5.7; LRMS (ESI-MS m/z): Mass calcd for $C_{20}H_{33}NO_4Si$ $[M]^+$, 379.57. Found 380.

Example 13

(R)-tert-butyl 3-hydroxy-1-oxo-1-phenylpropan-2-ylcarbamate (24): (R)-tert-butyl 3-(tert-butyldimethylsilyloxy)-1-oxo-1-phenylpropan-2-ylcarbamate (23) (1.5 g, 4.0 mmol, 1.0 equiv.) was added to a 100 mL RBF followed by a 1:1 mixture of THF/H$_2$O (20 mL). The mixture was stirred and glacial acetic acid (30 mL) was added to the reaction flask.

The reaction stirred for 22 h at rt. The reaction was transferred to a 500 mL separatory funnel with sat. NaCl (75 mL) and sat. NaHCO3 (50 mL). The aqueous layer was extracted with EtOAc (3×75 mL) and the combined organic layers were dried over Na$_2$SO$_4$. The solution was then concentrated on a rotary evaporator and dried under vacuum to give 1.3 g of crude material. The residue was purified by flash column chromatography (40% EtOAc/hexanes) to give 1.0 g (95%) of 24 as a colorless oil which crystallized to a white solid. R$_f$=0.27 (40% EtOAc/hexanes); mp=60-62° C.; $[\alpha]_D^{23.5}$=+12.4 (c 1.01, MeOH); IR (KBr) 3420, 2976, 2931, 1683, 1503, 1366, 1165, 1061 cm–; $^1$H NMR (500 MHz, CDCl$_3$) δ 8.00 (d, J=7.5 Hz, 2H, Ph-H), 7.62 (t, J=7.5 Hz, 1H, Ph-H), 7.51 (t, J=7.5 Hz, 2H, Ph-H), 5.88 (br s, 1H, carbamate-NH), 5.35 (br s, 1H, Boc-NH—CH), 4.02 (m, 1H, CH—CH$_2$), 3.86 (m, 1H, CH—CH$_2$), 2.91 (br s, 1H, CH$_2$—OH), 1.47 (s, 9H, t-butyl-CH$_3$); $^{13}$C (125 MHz, CDCl$_3$) δ 197.4, 156.3, 134.6, 134.1, 129.0, 128.9, 80.5, 64.7, 58.1, 28.4; LRMS (ESI-MS m/z): Mass calcd for C$_{14}$H$_{19}$NNaO$_4$ [M+Na]$^+$, 288.29. Found 288.

Example 14

(R)-2-(tert-butoxycarbonyl)-3-oxo-3-phenylpropyl acetate (25): (R)-tert-butyl 3-hydroxy-1-oxo-1-phenylpropan-2-ylcarbamate (24) (800 mg, 3.0 mmol, 1.0 equiv.) was added to a 100 mL RBF followed by CH$_2$Cl$_2$ (30 mL). The resulting solution was cooled to 0° C. via an ice bath. Next, acetic anhydride (340 μL, 3.6 mmol, 1.2 equiv.), DIEA (630 μL, 3.6 mmol, 1.2 equiv.), and DMAP (36 mg, 0.3 mmol, 0.1 equiv.) were added to the reaction flask. The reaction solution stirred for 15 min at 0° C., was quenched with 1% HCl (50 mL), and transferred to a separatory funnel with CH$_2$Cl$_2$ (100 mL). The resulting organic layer was washed with 1% HCl (2×40 mL) and sat. NaCl (2×40 mL). The organic layer was dried over Na$_2$SO$_4$, concentrated on a rotary evaporator, and dried under vacuum to give 1.2 g of a crude colorless oil. The residue was purified by flash column chromatography (25% EtOAc/hexanes) (Note: Only if purification is necessary) to give 870 mg (96%) of 25 as a colorless oil. R$_f$=0.30 (25% EtOAc/hexanes); $[\alpha]_D^{23.5}$=+29.2 (c 0.30, MeOH); IR (film) 3343, 3354, 3062, 2976, 2933, 1745, 1713, 1687, 1506, 1366, 1230, 1164, 1053 cm$^{-1}$; $^1$H NMR (500 MHz, CDCl$_3$) δ 8.02 (d, J=7.5 Hz, 2H, Ph-H), 7.62 (t, J=7.5 Hz, 1H, Ph-H), 7.51 (t, J=7.5 Hz, 2H, Ph-H), 5.66 (d, J=8.0 Hz, 1H, carbamate-NH), 5.59 (m, 1H, Boc-NH—CH), 4.51 (dd, J=11.5, 4.0 Hz, 1H, CH—CH$_2$), 4.18 (dd, J=11.5, 6.0 Hz, 1H, CH—CH$_2$), 1.99 (s, 3H, O=C—CH$_3$), 1.46 (s, 9H, t-butyl-CH$_3$); $^{13}$C NMR (125 MHz, CDCl$_3$) δ 196.2, 170.9, 155.5, 134.6, 134.3, 129.1, 128.8, 80.3, 64.9, 54.6, 28.5, 20.8; LRMS (ESI-MS m/z): Mass calcd for C$_{16}$H$_{21}$NNaO$_5$ [M+Na]$^+$, 330.33. Found 330. Anal. calcd for C$_{16}$H$_{21}$NO$_5$: C, 62.53; H, 6.89; N, 4.56 Found: C, 62.19; H, 6.98; N, 4.48. Chiral analysis and separation was conducted on a Varian Workstation using a (S,S) WHELK-O Column eluting with a solvent system of 9:1 Hexanes:IPA at 1.5 mL/min.

Example 15

(R)-3-Acetoxy-1-oxo-1-phenylpropan-2-aminium chloride (8): (R)-2-(tertbutoxycarbonyl)-3-oxo-3-phenylpropyl acetate (25) (310 mg, 1.0 mmol, 1.0 equiv.) was added to a 100 mL RBF followed by a 4.0 N HCl-Dioxane solution (7.5 mL, 30.0 mmol, 30.0 equiv.). The solution was stirred for 15 min and a precipitate formed. Et$_2$O (50 mL) was added to the reaction flask and the precipitate was filtered with a Buchner funnel. The precipitate was then washed with an additional portion of Et$_2$O (50 mL) and dried under vacuum to give 190 mg (78%) of 8 as a white solid. Decomposition occurs at 164-166° C.; $^1$H NMR (500 MHz, DMSO) δ 8.94 (s, 3H, CH—NH$_3$) 8.09 (d, J=7.5 Hz, 2H, Ph-H), 7.73 (t, J=7.5 Hz, 1H, Ph-H), 7.59 (t, J=7.5 Hz, 2H, Ph-H), 5.47 (s, 1H, $^+$NH$_3$—CH), 4.60 (AB, J=12.5 Hz, 1H, CH—CH$_2$), 4.42 (A B, J=12.5 Hz, 1H, CH—CH$_2$) 1.94 (s, 3H, O=C—CH$_3$); $^{13}$C NMR (125 MHz, DMSO) δ 193.3, 169.9, 134.6, 133.3, 129.1, 128.7, 62.0, 54.3, 20.5; LRMS (ESI-MS m/z): Mass calcd for C$_{11}$H$_{14}$NO$_3$ [M+H]$^+$, 208.23. Found 208. Anal. calcd for C$_{11}$H$_{14}$ClNO$_3$: C, 54.22; H, 5.79; N, 5.75 Found: C, 54.13; H, 5.77; N, 5.69.

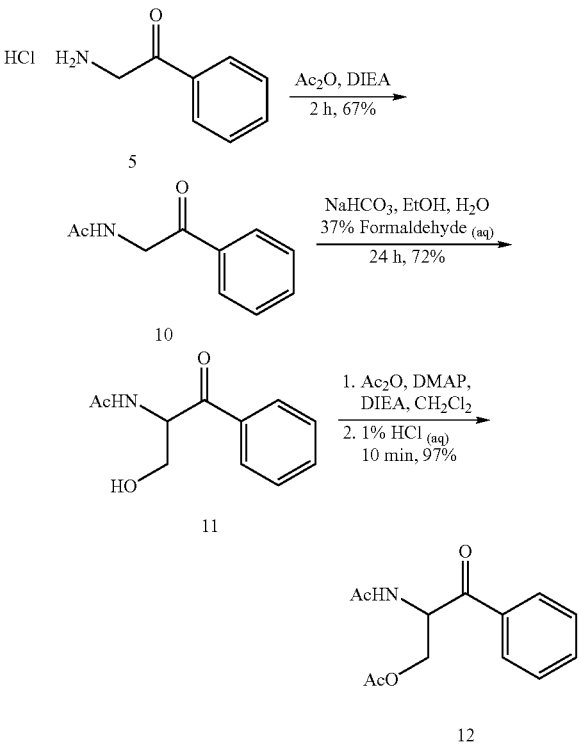

Example 16

N-(1-oxo-1-phenylethan-2-yl)acetamide (10): 2-oxo-2-phenylethanaminium chloride (5) (1.7 g, 10.0 mmol, 1.0 equiv.) was added to a 100 mL RBF followed by CH$_2$Cl$_2$ (50 mL). The resulting solution was cooled to 0° C. via an ice bath. Next, acetic anhydride (1.4 mL, 15.0 mmol, 15.0 equiv.) and DIEA (5.3 mL, 30.0 mmol, 30.0 equiv.) were added to the reaction flask. The reaction solution stirred for 2 h at 0° C. and was allowed to warm to rt. The solution was stirred at rt for 1 h. The solution was transferred to a separatory funnel with CH$_2$Cl$_2$ (90 mL). The resulting organic layer was washed with 1% HCl (2×50 mL) and sat. NaCl (2×50 mL). The organic layer was dried over Na$_2$SO$_4$, concentrated on a rotary evaporator, and dried under vacuum to give a yellowish solid. The solid was dissolved in EtOAc (15 mL) and precipitated during the slow addition of hexanes (30 mL). The precipitate that formed was dried under vacuum to give 1.3 g (74%) of 10 as a white solid. R$_f$=0.31 (100% EtOAc); mp=85-87° C.; IR (KBr) 3319, 3059, 2936, 2900, 1683, 1649, 1597, 1556, 1370, 1011 cm$^{-1}$; $^1$H NMR (500 MHz, CDCl$_3$) δ 7.98 (d, J=7.5 Hz, 2H, Ph-H), 7.63 (t, J=7.5 Hz, 1H, Ph-H), 7.50 (t, J=7.5 Hz, 2H, Ph-H), 6.69 (br s, 1H, Ac—NH), 4.78 (d, J=4.5 Hz, 2H, Ac—NH—CH$_2$), 2.12 (s, 3H, NH—COCH$_3$); $^{13}$C NMR (125 MHz, CDCl$_3$) δ 194.0, 170.5, 134.5, 134.3, 129.1, 128.1, 46.7, 23.2; LRMS (ESI-MS m/z): Mass calcd for C$_{10}$H$_{11}$NO$_2$ [M]$^+$, 177.20. Found 178. Anal. calcd for C$_{10}$H$_{11}$NO$_2$: C, 67.78; H, 6.26; N, 7.90 Found: C, 67.63; H, 6.29; N, 7.87. Spectroscopic data were consistent with the literature data for this compound.

Example 17

N-(3-hydroxy-1-oxo-1-phenylpropan-2-yl)acetamide (11): N-(1-oxo-1-phenylethan-2-yl)acetamide (10) (1.1 g, 6.0 mmol, 1.0 equiv.) was added to a 100 mL RBF followed by EtOH (25 mL, 200 proof). Next, a 0.5 M solution of NaHCO$_3$ (250 mg, 3.0 mmol, 0.5 equiv.) was added followed by a 37% solution of formaldehyde (730 μL, 9.0 mmol, 1.5 equiv.). The solution was stirred at rt. for 24 h and transferred to a separatory funnel with a 1.0 M solution of NaCl (2.9 g, 50.0 mmol). The solution was extracted with CH$_2$Cl$_2$ (5×60 mL). The organic layer was dried over Na$_2$SO$_4$, concentrated on a rotary evaporator, and dried under vacuum to give a crude off-white solid. The solid was washed with EtOAc (10 mL) to remove all impurities. The remaining solid was dried under vacuum to give 900 mg (72%) of 11 as a white solid. R$_f$=0.11 (5% MeOH/CH$_2$Cl$_2$); mp=115-117° C.; IR (KBr) 3312, 3262, 2915, 1696, 1639, 1537, 1228, 1101 cm$^{-1}$; $^1$H NMR (500 MHz, CDCl$_3$) δ 8.00 (d, J=7.0 Hz, 2H, Ph-H), 7.61 (t, J=7.0 Hz, 1H, Ph-H), 7.48 (t, J=7.0 Hz, 2H, Ph-H), 7.17 (d, J=7.0 Hz, 1H, Ac—NH), 5.63 (m, 1H, Ac—NH—CH), 4.01 (m, 1H, CH—CH$_2$), 3.88 (m, 1H, CH—CH$_2$), 2.06 (s, 3H, NH—COCH$_3$); $^{13}$C NMR (125 MHz, CDCl$_3$) δ 197.0, 171.2, 134.3, 129.1, 128.9, 64.4, 57.3, 23.2; LRMS (ESI-MS m/z): Mass calcd for C$_{11}$H$_{13}$NNaO$_3$ [M+Na]$^+$, 230.22 Found 208. Anal. calcd for C$_{11}$H$_{13}$NO$_3$: C, 63.76; H, 6.32; N, 6.76 Found: C, 63.92; H, 6.34; N, 6.74. Spectroscopic data were consistent with the literature data for this compound.

Example 18

N-(1-acetoxy-3-oxo-3-phenylpropyl)acetamide (12): N-(3-hydroxy-1-oxo-1-phenylpropan-2-yl)acetamide (11) (210 mg, 1.0 mmol, 1.0 equiv.) was added to a 100 mL RBF followed by CH$_2$Cl$_2$ (10 mL). The resulting solution was cooled to 0° C. via an ice bath. Next, acetic anhydride (110 μL, 1.2 mmol, 1.2 equiv.), DIEA (210 μL, 1.2 mmol, 1.2 equiv.), and DMAP (12 mg, 0.1 mmol, 0.1 equiv.) were added to the reaction flask. The reaction solution stirred for 15 min at 0° C., was quenched with 1% HCl (25 mL), and transferred to a separatory funnel with CH$_2$Cl$_2$ (60 mL). The resulting organic layer was washed with 1% HCl (2×20 mL) and sat. NaCl (2×20 mL). The organic layer was dried over Na$_2$SO$_4$, concentrated on a rotary evaporator, and dried under vacuum to give 240 mg (97%) of 12 as a white solid. R$_f$=0.30 (5% MeOH/CH$_2$Cl$_2$); MP=82-83° C.; IR (KBr) 3312, 3065, 2939, 1730, 1687, 1647, 1537, 1372, 1259 cm$^{-1}$; $^1$H NMR (500 MHz, CDCl$_3$) δ 8.02 (d, J=8.0 Hz, 2H, Ph-H), 7.64 (t, J=7.5 Hz, 1H, Ph-H), 7.52 (t, J=7.5 Hz, 2H, Ph-H), 6.60 (br d, J=6.5 Hz, 1H, Ac—NH), 5.86 (m, 1H, Ac—NH—CH), 4.52 (dd, J=12.0, 4.0 Hz, 1H, CH—CH$_2$), 4.26 (dd, J=12.0, 4.0 Hz, 1H, CH—CH$_2$), 2.09 (s, 3H, NH—COCH$_3$), 1.98 (s, 3H, OCOCH$_3$); $^{13}$C NMR (125 MHz, CDCl$_3$) δ 196.0, 170.8, 170.1, 134.4, 134.3, 129.2, 128.9, 64.5, 53.4, 23.2, 20.7; LRMS (ESI-MS m/z): Mass calcd for C$_{13}$H$_{15}$NO$_5$ [M]$^+$, 249.26. Found 250. Anal. calcd for C$_{13}$H$_{15}$NO$_4$: C, 62.64; H, 6.07; N, 5.62 Found: C, 62.55; H, 6.07; N, 5.53. Spectroscopic data were consistent with the literature data for this compound.

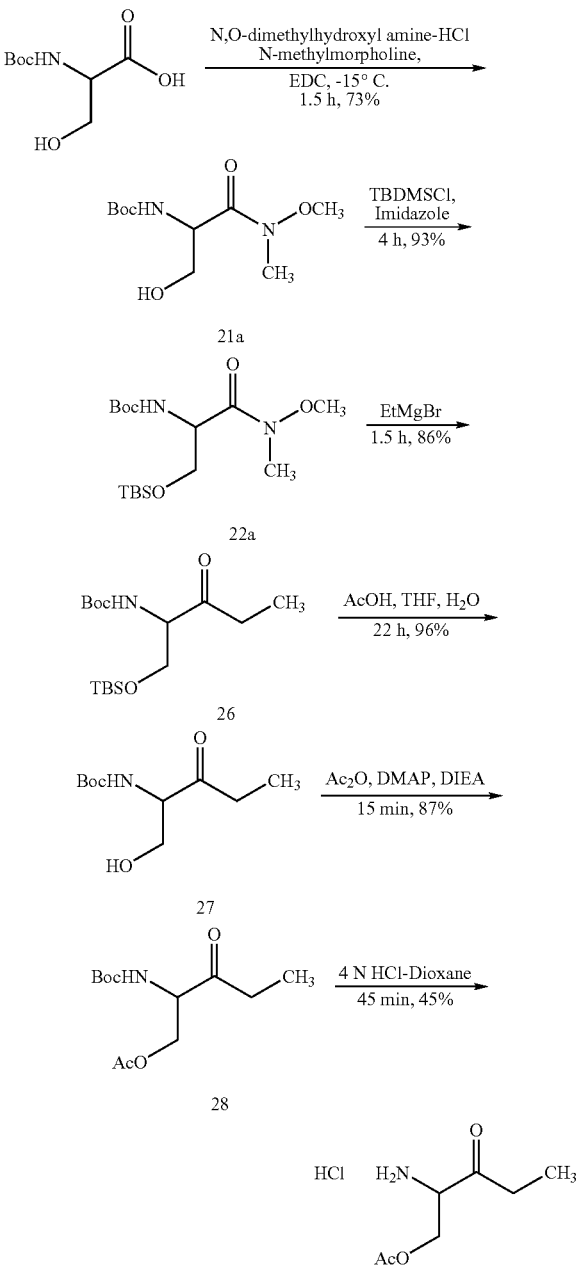

Racemic Ethyl Ketone Synthesis (13)

Example 19

Tert-butyl 3-hydroxy-1-(methoxy(methyl)amino)-1-oxo-propan-2-ylcarbamate (21a): 2-(tert-butoxycarbonyl)-3-hydroxypropanoic acid (5.0 g, 24.4 mmol, 1.0 equiv.) was added to a 250 mL RBF followed by CH$_2$Cl$_2$ (90 mL) and cooled to −15° C. via an ice/salt water bath. Next, N,O-dimethylhydroxyl amine-HCl (2.5 g, 25.6 mmol, 1.1 equiv.)

and N-methylmorpholine (2.8 mL, 25.6 mmol, 1.1 equiv.) were added to the reaction flask. EDC (4.9 g, 25.6 mmol, 1.1 equiv.) was then added to the reaction flask in 5 equal portions over the first 30 min (1 portion per 6 min). After completely charged with EDC, the reaction was allowed to stir an additional 1 h at −15° C. The reaction was quenched with ice cold 1% HCl (25 mL) and transferred to a separatory funnel with $CH_2Cl_2$ (100 mL). The mixture was washed with 1% HCl (3×30 mL), sat. $NaHCO_3$ (2×30 mL), and sat. NaCl (1×30 mL). The organic layer was separated and dried over $Na_2SO_4$. The solution was concentrated on a rotary evaporator and dried under vacuum to give 4.40 g (73%) of 21a as a white solid. $R_f$=0.36 (100% EtOAc); mp=115-116° C.; IR (KBr) 3470, 3354, 2977, 2943, 1703, 1645, 1538, 1363, 1180, 1078, 1064 cm$^{-1}$; $^1$H NMR (500 MHz, CDCl$_3$) δ 5.66 (br d, J=6.0 Hz, 1H, carbamate-NH), 4.81 (br s, 1H, Boc-NH—CH), 3.82 (m, 2H, CH—CH$_2$), 3.79 (s, 3H, N—OCH$_3$), 3.24 (s, 3H, N—CH$_3$), 2.86 (br s, 1H, CH$_2$—OH), 1.45 (s, 9H, t-butyl-CH$_3$); $^{13}$C (125 MHz, CDCl$_3$) δ 171.1, 156.1, 80.2, 63.9, 61.8, 52.6, 32.3, 28.5; LRMS (ESI-MS m/z): Mass calcd for $C_{10}H_{20}N_2O_5$ [M]$^+$, 248.28. Found 249. Spectroscopic data were consistent with the literature data for this compound.

Example 20

Tert-butyl 3-(tert-butyldimethylsilyloxy)-1 (methoxy(methyl)amino)-1-oxopropan-2-ylcarbamate (22a): tert-butyl 3-hydroxy-1-(methoxy(methyl)amino)-1-oxopropan-2-ylcarbamate (21a) (4.4 g, 17.5 mmol, 1.0 equiv.) was added to a 100 mL RBF followed by DMF (35 mL) and cooled to 0° C. via an ice bath. Next, TBDMSCl (2.90 g, 19.3 mmol, 1.1 equiv.) and imidazole (2.40 g, 35.1 mmol, 2.0 equiv.) were added to the reaction flask. The solution was stirred at 0° C. for 1 h and then allowed to warm to rt, stirring an additional 2 h. The reaction solution was transferred to a 500 mL separatory funnel with EtOAc (150 mL). The mixture was washed with 1% HCl (3×40 mL), sat. $NaHCO_3$ (1×40 mL), and sat. NaCl (2×40 mL). The organic layer was separated and dried over $Na_2SO_4$. The solution was concentrated on a rotary evaporator and dried under vacuum to give 5.9 g (93%) of 22a as an oil which crystallized to a white solid upon standing. $R_f$=0.54 (50% EtOAc/hexanes); mp=71-72° C.; IR (film) 3437, 3324, 2953, 2929, 2884, 2856, 1715, 1666, 1496, 1471, 1365, 1253, 1171, 1114 cm$^{-1}$; $^1$H NMR (500 MHz, CDCl$_3$) δ 5.34 (br d, J=8.5 Hz, 1H, carbamate-NH), 4.73 (br s, 1H, Boc-NH—CH), 3.83 (m, 1H, CH—CH$_2$), 3.77 (m, 1H, CH—CH$_2$), 3.73 (s, 3H, N—OCH$_3$), 3.19 (s, 3H, N—CH$_3$), 1.41 (s, 9H, Boc-t-butyl-CH$_3$), 0.84 (s, 9H, Si-t-butyl-CH$_3$), 0.00 (s, 6H, Si—(CH$_3$)$_2$); $^{13}$C NMR (125 MHz, CDCl$_3$) δ 170.9, 155.5, 79.7, 63.6, 61.6, 52.6, 32.3, 28.5, 25.9, 18.4, −5.4; LRMS (ESI-MS m/z): Mass calcd for $C_{16}H_{34}N_2O_5Si$ [M]$^+$, 362.54. Found 363.

Example 21

Tert-butyl 1-(tert-butyldimethylsilyloxy)-3-oxopentan-2-ylcarbamate (26): tert-butyl 3-(tert-butyldimethylsilyloxy)-1-(methoxy(methyl)amino)-1-oxopropan-2-ylcarbamate (22a) (1.5 g, 4.0 mmol, 1.0 equiv.) was added to a 100 mL RBF followed by THF (33 mL). The mixture was cooled to 0° C. via an ice bath and a 1.0 M solution of EtMgBr in THF (12.0 mL, 12.0 mmol, 3.0 equiv.) was added over 10 min. The reaction stirred for 30 min at 0° C. and the ice bath was removed. The reaction stirred for an additional 1.0 h at rt. and was again cooled to 0° C. via an ice bath. Next, the reaction was quenched by addition of 1.0 M HCl (33 mL). The solution was transferred to a separatory funnel with additional 1.0 M HCl (20 mL) and extracted with EtOAc (3×40 mL). The organic layers were washed with sat. NaCl (2×30 mL) and dried over $Na_2SO_4$. The solution was then concentrated on a rotary evaporator and dried under vacuum to give 1.4 g of crude material. The residue was purified by flash column chromatography (10% EtOAc/hexanes) to give 1.1 g (86%) of 26 as a clear oil. $R_f$=0.25 (10% EtOAc/hexanes); IR (film) 3431, 3371, 2975, 2953, 2930, 2883, 2856, 1711, 1492, 1172, 838 cm$^{-1}$; $^1$H NMR (500 MHz, CDCl$_3$) δ 5.45 (d, J=7.0 Hz, 1H, carbamate-NH), 4.22 (m, 1H, Boc-NH—CH), 4.00 (dd, J=10.0, 3.5 Hz, 1H, CH—CH$_2$), 3.76 (dd, J=10.0, 4.0 Hz, 1H, CH—CH$_2$), 2.56 (m, 1H, O=C—CH$_2$), 2.44 (m, 1H, O=C—CH$_2$), 1.39 (s, 9H, Boc-tbutyl-CH$_3$), 1.08 (t, J=7.0 Hz, 3H, O=C—CH$_2$CH$_3$), 0.79 (s, 9H, Si-t-butyl-CH$_3$), −0.03 (s, 6H, Si—CH$_3$); $^{13}$C NMR (125 MHz, CDCl$_3$) δ 208.5, 155.5, 79.7, 63.6, 61.2, 33.5, 28.4, 25.8, 18.2, 7.5, −5.5, −5.5; LRMS (ESI-MS m/z): Mass calcd for $C_{16}H_{33}NO_4Si$ [M]$^+$, 331.52. Found 332.

Example 22

Tert-butyl 1-hydroxy-3-oxopentan-2-ylcarbamate (27): tert-butyl 1-(tertbutyldimethylsilyloxy)-3-oxopentan-2-ylcarbamate (26) (900 mg, 2.7 mmol, 1.0 equiv.) was added to a 100 mL RBF followed by a 1:1 mixture of THF/H$_2$O (14 mL). The mixture was stirred and glacial acetic acid (21 mL) was added to the reaction flask. The reaction stirred for 22 h at rt. The reaction was transferred to a 250 mL separatory funnel with sat. NaCl (50 mL) and sat. $NaHCO_3$ (30 mL). The aqueous layer was extracted with EtOAc (3×75 mL) and the combined organic layers were dried over $Na_2SO_4$. The solution was then concentrated on a rotary evaporator and dried under vacuum to give 825 mg of crude oil. The residue was purified by flash column chromatography (50% EtOAc/hexanes) to give 570 mg (96%) of 27 as a colorless oil. $R_f$=0.31 (50% EtOAc/hexanes); IR (film) 3420, 2976, 2937, 1686, 1498, 1365, 1163, 1056 cm$^{-1}$; $^1$H NMR (500 MHz, CDCl$_3$) δ 5.78 (d, J=6.0 Hz, 1H, carbamate-NH), 4.34 (br s, 1H, Boc-NH—CH), 3.97 (d, J=10.0 Hz, 1H, CH—CH$_2$), 3.87 (d, J=10.0 Hz, 1H, CH—CH$_2$), 3.34 (br s, 1H, CH$_2$—OH), 2.66 (m, 1H, O=C—CH$_2$), 2.59 (m, 1H, O=CCH$_2$), 1.45 (s, 9H, t-butyl-CH$_3$), 1.09 (t, J=7.0 Hz, 3H, O=C—CH$_2$CH$_3$); $^{13}$C NMR (125 MHz, CDCl$_3$) δ 209.0, 156.1, 80.3, 63.1, 61.5, 33.4, 28.4, 7.5.

Example 23

2-(Tert-butoxycarbonyl)-3-oxopentyl acetate (28): tert-butyl 1-hydroxy-3-oxopentan-2-ylcarbamate (27) (440 mg, 2.0 mmol, 1.0 equiv.) was added to a 100 mL RBF followed by $CH_2Cl_2$ (20 mL). The resulting solution was cooled to 0° C. via an ice bath. Next, acetic anhydride (230 μL, 2.5 mmol, 1.2 equiv.), DIEA (430 μL, 2.5 mmol, 1.2 equiv.), and DMAP (25 mg, 0.2 mmol, 0.1 equiv.) were added to the reaction flask. The reaction solution stirred for 15 min at 0° C., was quenched with 1% HCl (30 mL), and transferred to a separatory funnel with $CH_2Cl_2$ (90 mL). The resulting organic layer was washed with 1% HCl (2×30 mL) and sat. NaCl (2×30 mL). The organic layers were dried over $Na_2SO_4$, concentrated on a rotary evaporator, and dried under vacuum to give 550 mg (87%) of 28 as a colorless oil. $R_f$=0.59 (50% EtOAc/hexanes); IR (film) 3366, 2878, 1746, 1711, 1367, 1234, 1166 cm$^{-1}$; $^1$H NMR (500 MHz, CDCl$_3$) δ 5.54 (d, J=6.0 Hz, 1H, carbamate-NH), 4.54 (t, J=4.0 Hz, 1H, Boc-NH—CH), 4.47 (dd, J=11.5, 3.5 Hz, 1H, CH—CH$_2$), 4.34 (dd, J=11.5, 3.5 Hz, 1H, CH—CH$_2$), 2.62 (m, 1H, O═C—CH$_2$), 2.56 (m, 1H, O═C—CH$_2$), 2.04 (s, 3H, O═C—CH$_3$), 1.45 (s, 9H, t-butyl-CH$_3$), 1.09 (t, J=7.0 Hz, 3H, O═C—CH$_2$CH$_3$); $^{13}$C NMR (125 MHz, CDCl$_3$) δ 206.9, 170.6, 155.3, 80.2, 63.7, 58.6, 33.2, 28.3, 20.7, 7.5; LRMS (ESI-MS m/z): Mass calcd for C$_{12}$H$_{21}$NNaO$_5$ [M+Na]$^+$, 282.29. Found 282.

Example 24

1-Acetoxy-3-oxopentan-2-aminium chloride (13): 2-(tert-butoxycarbonyl)-3-oxopentyl acetate (28) (310 mg, 1.0 mmol, 1.0 equiv.) was added to a 25 mL RBF followed by a 4.0 N HCl-Dioxane solution (1.8 mL, 7.0 mmol, 7.0 equiv.). The solution was stirred for 45 min and the dioxane was evaporated. The resulting residue was taken up in Et$_2$O (10 mL). A precipitate formed and was filtered with a Buchner funnel. The precipitate was then washed with an additional portion of Et$_2$O (25 mL) and dried under vacuum to give 88 mg (45%) of 13 as a white solid. Decomposition occurs at 119-122° C.; 1H NMR (500 MHz, DMSO) δ 8.77 (s, 3H, CH—NH$_3$) 4.53 (br s, 1H, $^+$NH$_3$—CH), 4.53 (br s, 1H, CH—CH$_2$), 4.45 (s, 1H, CH—CH$_2$) 2.65 (br q, J=5.0 Hz, 2H, O═C—CH$_2$), 1.99 (s, 3H, O═C—CH$_3$), 0.93 (t, J=7.0 Hz, 3H, O═C—CH$_2$CH$_3$); $^{13}$C NMR (125 MHz, DMSO) δ 204.2, 170.1, 61.1, 57.1, 32.0, 20.6, 7.1; LRMS (ESI-MS m/z): Mass calcd for C$_7$H$_{14}$NO$_3$ [M]$^+$, 160.19. Found 160. Anal. calcd for C$_7$H$_{14}$ClNO$_3$: C, 42.97; H, 7.21; N, 7.16 Found: C, 42.53; H, 7.23; N, 7.46.

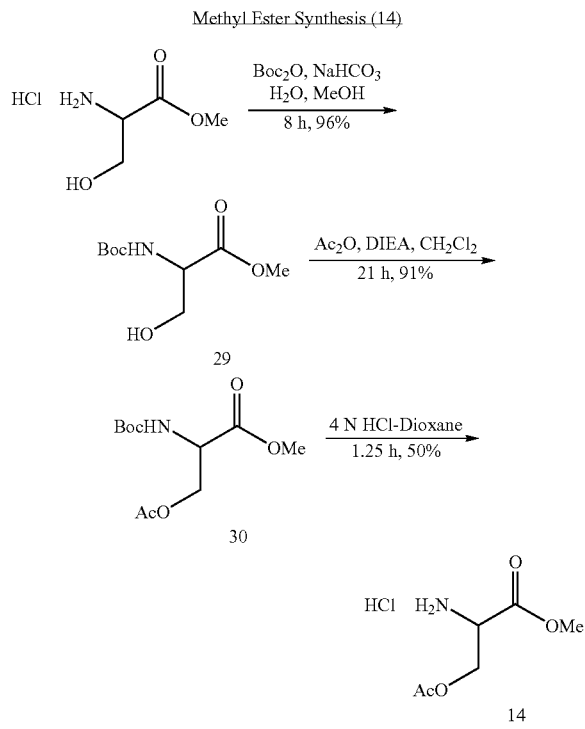

Example 25

Methyl 2-(tert-butoxycarbonyl)-3-hydroxypropanoate (29): 3-hydroxy-1-methoxy-1-oxopropan-2-aminium chloride (5.0 g, 32.0 mmol, 1.0 equiv.) and NaHCO$_3$ (6.7 g, 80.0 mmol, 2.5 equiv.) were added to a 500 mL RBF followed by dH$_2$O (96 mL) and MeOH (96 mL). Next, Boc$_2$O (10.5 g, 48.0 mmol, 1.5 equiv.) was added to the reaction flask. The reaction was stirred for 8 h and the MeOH was evaporated on a rotary evaporator. The remaining aqueous layer was acidified with 0.5 M HCl (200 mL), transferred to a separatory funnel with EtOAc (100 mL) and extracted with EtOAc (3×100 mL). The organic layers were then washed with 20% NaHCO$_3$ (1×100 mL) and sat. NaCl (1×100 mL). The organic layers were combined and dried over Na$_2$SO$_4$, concentrated on a rotary evaporator, and dried under vacuum to give 6.80 g (96%) of 29 as a colorless oil. R$_f$=0.61 (100% EtOAc); IR (film) 3389, 2976, 1743, 1691, 1159, 1058 cm$^{-1}$; $^1$H NMR (500 MHz, CDCl$_3$) δ 5.61 (d, J=7.5 Hz, 1H, carbamate-NH), 4.38 (br s, 1H, Boc-NH—CH), 3.96 (m, 1H, CH—CH$_2$), 3.88 (m, 1H, CH—CH$_2$), 3.78 (s, 3H, OCH$_3$), 3.12 (br s, 1H, CH$_2$OH), 1.45 (s, 9H, t-butyl-CH$_3$); $^{13}$C NMR (125 MHz, CDCl$_3$) δ 171.6, 155.9, 80.4, 63.5, 55.8, 52.8, 28.4; LRMS (ESI-MS m/z): Mass calcd for C$_9$H$_{17}$NNaO$_5$ [M+Na]$^+$, 242.22. Found 242. Spectroscopic data were consistent with the literature data for this compound.

Example 26

Methyl 3-acetoxy-2-(tert-butoxycarbonyl)propanoate (30): methyl 2-(tertbutoxycarbonyl)-3-hydroxypropanoate (29) (2.2 g, 10.0 mmol, 1.0 equiv.) was added to a 100 mL RBF followed by CH$_2$Cl$_2$ (40 mL). Next, DIEA (2.1 mL, 12.0 mmol, 1.2 equiv.) and acetic anhydride (1.2 mL, 13.0 mmol, 1.3 equiv.) were added to the reaction mixture and the solution was stirred at rt. The reaction solution was stirred for a total of 21 h. The solution was transferred to a separatory funnel with CH$_2$Cl$_2$ (75 mL), washed with 1% HCl (2×50 mL), and sat. NaCl (2×50 mL). The organic layers were dried over Na$_2$SO$_4$, concentrated on a rotary evaporator, and dried under vacuum to give 2.4 g (91%) of 30 as a clear oil which crystallized to a white solid upon standing. R$_f$=0.37 (25% EtOAc/hexanes); mp=61-62° C.; IR (KBr) 3327, 2985, 1742, 1683, 1533, 1348, 1241, 1166, 1071, 1038 cm$^{-1}$; $^1$H NMR (500 MHz, CDCl$_3$) δ 5.33 (br d, J=8.0 Hz, 1H, carbamate-NH), 4.58 (m, 1H, Boc-NH—CH), 4.44 (dd, J=11.0, 3.5 Hz, 1H, CH—CH$_2$), 4.33 (dd, J=11.0, 3.5 Hz, 1H, CH—CH$_2$), 3.78 (s, 3H, OCH$_3$), 2.06 (s, 3H, O═C—CH$_3$), 1.46 (s, 9H, t-butyl-CH$_3$).; $^{13}$C NMR (125 MHz, CDCl$_3$) δ 170.6, 170.5, 155.3, 80.5, 64.5, 53.0, 52.9, 28.4, 20.8; LRMS (ESI-MS m/z): Mass calcd for C$_{11}$H$_{19}$NNaO$_6$ [M+Na]$^+$, 284.26. Found 284.

Example 27

3-Acetoxy-1-methoxy-1-oxopropan-2-aminium chloride (14): methyl 3-acetoxy-2-(tert-butoxycarbonyl)propanoate (30) (990 mg, 3.8 mmol, 1.0 equiv) was added to a 50 mL RBF followed by Et$_2$O (5 mL). The resulting solution was cooled to 0° C., and a 4 N HCl-Dioxane solution (8.0 mL, 32.0 mmol, 8.5 equiv.) was added. The ice bath was removed and the solution was stirred for 1.25 h while warming to rt. The solvent was evaporated with a steady stream of N$_{2\,(g)}$. The resulting residue was taken up in Et$_2$O (15 mL) and a white precipitate formed. The mixture was filtered, washed with Et$_2$O (3×25 mL), and dried under vacuum to give 370 mg (50%) of 14 as a white solid. mp=130-133° C.; $^1$H NMR (500 MHz, DMSO) δ 8.98 (s, 3H, CH—NH$_3$), 4.49 (dd, J=12.0, 3.0 Hz, 1H, CH—CH$_2$), 4.42 (t, J=4.0 Hz, 1H, $^+$NH$_3$—CH), 4.37 (dd, J=12.0, 3.0 Hz, 1H, CH—CH$_2$), 3.75 (s, 3H, OCH$_3$), 2.04 (s, 3H, O═CCH$_3$); $^{13}$C NMR (125 MHz, DMSO) δ 170.0, 167.6, 61.2, 53.1, 51.2, 20.6; LRMS (ESI-MS m/z): Mass calcd for C$_6$H$_{12}$NO$_4$ [M]$^+$, 162.16.

Found 162. Anal. calcd for $C_6H_{12}ClNO_4$: C, 36.47; H, 6.12; N, 7.09 Found: C, 36.71; H, 6.35; N, 6.98.

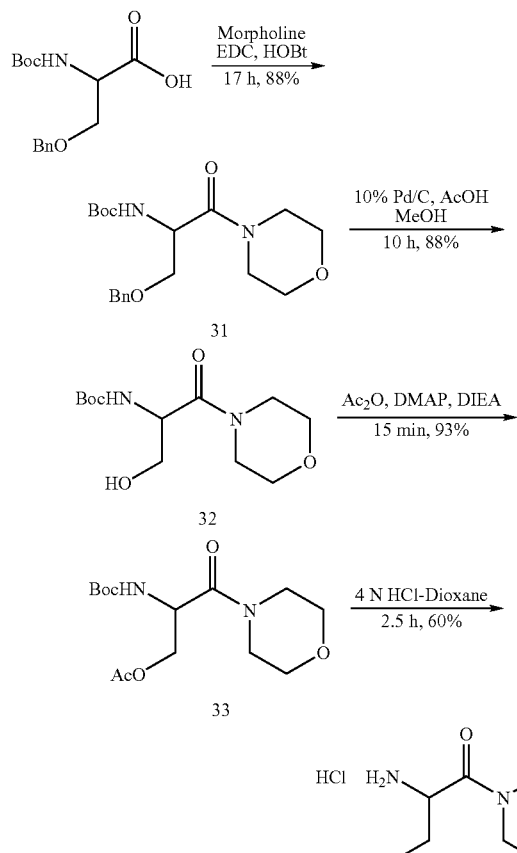

Morpholine Amide Synthesis of 15

31

32

33

15

Example 28

Tert-butyl 3-(benzyloxy)-1-morpholino-1-oxopropan-2-ylcarbamate (31): 3-(benzyloxy)-2-(tert-butoxycarbonyl)propanoic acid (2.3 g, 7.8 mmol, 1.0 equiv.) was added to a 100 mL RBF followed by $CH_2Cl_2$ (49 mL). Next, the reaction flask was cooled to 0° C. via an ice bath and EDC (1.8 g, 9.4 mmol, 1.2 equiv.) and HOBt (1.3 g, 9.4 mmol, 1.2 equiv.) were added as solids. Once all starting materials dissolved, morpholine was added (3.4 mL, 38.9 mmol, 5.0 equiv.) over 5 min. The solution was stirred for 1 h at 0° C., the ice bath was taken off, and the solution stirred for an additional 17 h at rt. The reaction mixture was transferred to a separatory funnel with $CH_2Cl_2$ (100 mL). The mixture was washed with 1% HCl (3×40 mL), sat. $NaHCO_3$ (2×40 mL), and sat. NaCl (2×40 mL). The organic layer was dried over $Na_2SO_4$, concentrated on a rotary evaporator, and dried under vacuum to give 2.7 of crude material. The residue was purified by flash column chromatography (60% EtOAc/hexanes) to give 2.5 g (88%) of 31 as a colorless oil which crystallized to a white solid. $R_f$=0.35 (60% EtOAc/hexanes); mp=87-88° C.; IR (KBr) 3452, 3311, 2974, 2927, 2860, 1702, 1648, 1495, 1452, 1166, 1115 cm$^{-1}$; $^1$H NMR (500 MHz, CDCl$_3$) δ 7.33 (m, 2H, Ph-$\underline{H}$), 7.28 (m, 3H, Ph-$\underline{H}$), 5.57 (d, J=8.0 Hz, 1H, carbamate-N$\underline{H}$), 4.82 (br q, J=5.5 Hz, 1H, Boc-NH—C$\underline{H}$), 4.49 (q, J=9.5 Hz, 2H, Ph-C$\underline{H}_2$), 3.77-3.40 (m, 10H, morpholine C$\underline{H}_2$'s & CH—C$\underline{H}_2$), 1.43 (s, 9H, t-butyl-C$\underline{H}_3$). $^{13}$C NMR (125 MHz, CDCl$_3$) δ 169.3, 155.2, 137.6, 128.5, 128.0, 127.9, 79.9, 73.5, 71.1, 66.7, 49.6, 46.3, 42.6, 28.4; LRMS (ESI-MS m/z): Mass calcd for $C_{19}H_{28}N_2NaO_5$ [M+Na]$^+$, 387.43. Found 387.

Example 29

Tert-butyl 3-hydroxy-1-morpholino-1-oxopropan-2-ylcarbamate (32): tert-butyl-3-(benzyloxy)-1-morpholino-1-oxopropan-2-ylcarbamate (31) (1.4 g, 4.0 mmol, 1.0 equiv.) was added to a 250 mL RBF followed by MeOH (40 mL). The reaction flask was flushed with $N_{2\ (g)}$ and charged with 10% Pd/C (290 mg). The flask was equiptpd with 2 $H_{2\ (g)}$ balloons and stirred at rt for 30 min. AcOH (230 μL, 4.0 mmol, 1.0 equiv) was then added and the reaction was allowed to stir for 10 h. The solution was filtered through a pad of celite, washing with additional MeOH (200 mL). The solution was concentrated on a rotary evaporator, and dried under vacuum to give 1.2 g of crude material. The residue was purified by flash column chromatography (100% EtOAc) to give 970 mg (88%) of 32 as a colorless oil which crystallized to a white solid. $R_f$=0.26 (100% EtOAc); mp=45-47° C.; IR (film) 3418, 3315, 2972, 2927, 2859, 1706, 1631, 1444, 1166 cm$^{-1}$; $^1$H NMR (500 MHz, CDCl$_3$) δ 5.87 (d, J=8.5 Hz, 1H, carbamate-N$\underline{H}$), 4.67 (br d, J=4 Hz, 1H, Boc-NH—C$\underline{H}$), 3.79 (br s, 2H, CH—C$\underline{H}_2$), 3.68-3.62 (m, 9H, morpholine C$\underline{H}_2$'s & O$\underline{H}$), 1.44 (s, 9H, t-butyl-C$\underline{H}_3$); $^{13}$C NMR (125 MHz, CDCl$_3$) δ 169.7, 155.7, 80.2, 66.8, 66.7, 64.0, 51.4, 46.3, 42.6, 28.4.

Example 30

2-(Tert-butoxycarbonyl)-3-morpholino-3-oxopropyl acetate (33): tert-butyl-3-hydroxy-1-morpholino-1-oxopropan-2-ylcarbamate (32) (550 mg, 2.0 mmol, 1.0 equiv.) was added to a 100 mL RBF followed by $CH_2Cl_2$ (20 mL). The resulting solution was cooled to 0° C. via an ice bath. Next, acetic anhydride (250 μL, 2.6 mmol, 1.3 equiv.), DIEA (420 μL, 2.4 mmol, 1.2 equiv.), and DMAP (24 mg, 0.2 mmol, 0.1 equiv.) were added to the reaction flask. The reaction solution stirred for 15 min at 0° C., was quenched with 1% HCl (30 mL), and transferred to a separatory funnel with $CH_2Cl_2$ (100 mL). The resulting organic layer was washed with 1% HCl (2×30 mL) and sat. NaCl (2×30 mL). The organic layer was dried over $Na_2SO_4$, concentrated on a rotary evaporator, and dried under vacuum to give 590 mg (93%) of 33 as a colorless oil. $R_f$=0.50 (100% EtOAc); IR (film) 3420, 3314, 2974, 2928, 2858, 1743, 1710, 1648, 1441, 1226, 1166 cm$^{-1}$; $^1$H NMR (500 MHz, CDCl$_3$) δ 5.66 (d, J=9.0 Hz, 1H, carbamate-N$\underline{H}$), 4.81 (br q, J=4.5 Hz, 1H, Boc-NH—C$\underline{H}$), 4.18 (m, 1H, CH—C$\underline{H}_2$), 3.93 (m, 1H, CH—C$\underline{H}_2$), 3.57 (m, 8H, morpholine C$\underline{H}_2$'s), 1.96 (s, 3H, O=C—C$\underline{H}_3$), 1.34 (s, 9H, t-butyl-C$\underline{H}_3$); $^{13}$C NMR (125 MHz, CDCl$_3$) δ 170.8, 167.5, 155.3, 79.8, 66.6, 64.4, 49.1, 46.0, 42.5, 28.2, 20.7; LRMS (ESI-MS m/z): Mass calcd for $C_{14}H_{24}N_2NaO_6$ [M+Na]$^+$, 339.34. Found 339.

Example 31

3-Acetoxy-1-morpholino-1-oxopropan-2-aminium chloride (15): 2-(tertbutoxycarbonyl)-3-morpholino-3-oxopropyl acetate (33) (95 mg, 0.3 mmol, 1.0 equiv) was added to a 50 mL RBF and 4.0 N HCl-Dioxane solution (8 mL, 32.0 mmol, 106 equiv.) was added. The solution was stirred for 2.5 h and the solvent was evaporated with a steady stream of $N_{2\ (g)}$. The resulting residue was taken up in $Et_2O$ (20 mL). The suspension was filtered, washed with $Et_2O$ (3×25 mL), and dried under vacuum to give 50 mg (60%) of 15 as a white solid. mp=154-155° C.; $^1$H NMR (500 MHz, DMSO) δ 8.49 (s, 3H, CH—N$\underline{H}_3$), 4.67 (s, 1H, $^+$NH$_3$—C$\underline{H}$), 4.28 (m, 2H, CH—C$\underline{H}_2$), 3.57-3.44 (m, 8H, morpholine C $\underline{H}_2$'s), 2.05 (s, 3H, O=C—C$\underline{H}_3$); $^{13}$C NMR (125 MHz, DMSO) δ 170.1, 164.4, 65.9, 61.1, 48.9, 45.5, 42.3, 20.7; LRMS (ESI-MS m/z): Mass calcd for $C_9H_{17}N_2O_4$ [M]$^+$, 217.24. Found 217, 433. Anal. calcd for $C_9H_{17}ClN_2O_4$: C, 42.78; H, 6.78; N, 11.09 Found: C, 42.59; H, 6.82; N, 10.90.

N-Methyl Synthesis of 16

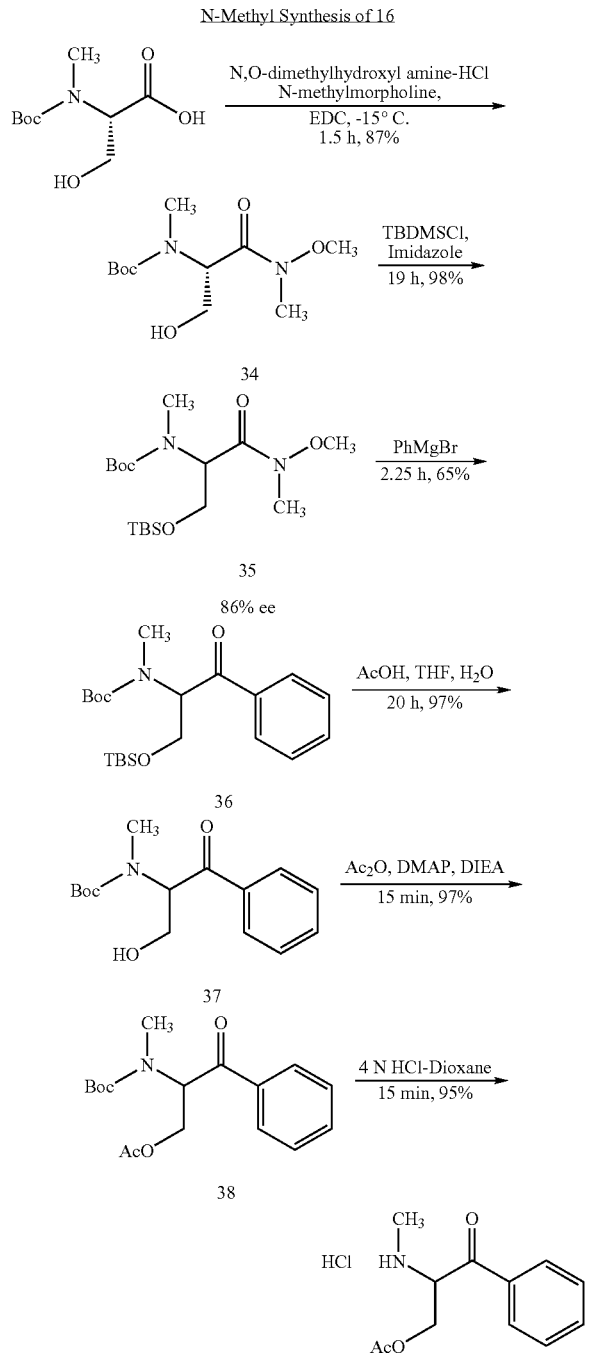

Example 32

Tert-butyl (S)-1-(N-methoxy-N-methylcarbamoyl)-2 hydroxyethylmethylcarbamate (34): tert-butyl (S)-1-carboxy-3-hydroxypropan-2-ylmethylcarbamate (3.3 g, 15.0 mmol, 1.0 equiv.) was added to a 200 mL RBF followed by CH$_2$Cl$_2$ (55 mL) and cooled to −15° C. via an ice/salt water bath. Next, N,O-dimethylhydroxyl amine-HCl (1.5 g, 15.8 mmol, 1.1 equiv.) and N-methylmorpholine (1.7 mL, 15.8 mmol, 1.05 equiv) were added to the reaction flask. EDC (3.0 g, 15.8, 1.1 equiv.) was then added to the reaction flask in 5 equal portions over the first 30 min (1 portion per 6 min). After the reaction flask was charged completely with EDC, the reaction was allowed to stir an additional hour at −15° C. The reaction was quenched with ice cold 1% HCl (25 mL) and transferred to a separatory funnel with CH$_2$Cl$_2$ (100 mL). The mixture was washed with 1% HCl (2×50 mL), sat. NaHCO$_3$ (1×50 mL), and sat. NaCl (2×50 mL). The organic layer was separated and dried over Na$_2$SO$_4$. The solution was concentrated on a rotary evaporator and dried under vacuum to give 3.4 g (87%) of 34 as a colorless oil. $R_f$=0.42 (100% EtOAc); $[\alpha]_D^{23.5}$=−60.9 (c 1.35, MeOH); IR (film) 3439, 2973, 2935, 1654, 1441, 1365, 1145, 1051 cm$^{-1}$; $^1$H NMR (500 MHz, CDCl$_3$) Major rotamer: δ 5.01 (br s, 1H, Boc-N—C$\underline{H}$), 3.97 (m, 1H, CH—C$\underline{H}_2$), 3.78 (m, 1H, CH—C$\underline{H}_2$), 3.71 (s, 3H, N—OC$\underline{H}_3$), 3.24 (s, 3H, N—C $\underline{H}_3$), 2.92 (br s, 1H, CH$_2$—O$\underline{H}$), 2.86 (Boc-N—C$\underline{H}_3$), 1.47 (s, 9H, Boc-t-butyl-C$\underline{H}_3$). Minor rotamer: 4.77 (br s, 1H, Boc-N—C$\underline{H}$), 3.69 (s, 3H, N—OC$\underline{H}_3$); $^{13}$C NMR (125 MHz, CDCl$_3$) Major rotamer: δ 171.4, 156.1, 80.3, 61.4, 60.9, 58.1, 56.6, 31.9, 28.4; LRMS (ESI-MS m/z): Mass calcd for $C_{11}H_{22}N_2O_5$ [M]$^+$, 262.30. Found 263.

Example 33

Tert-butyl 3-(tert-butyldimethylsilyloxy)-1 (methoxy(methyl)amino)-1-oxopropan-2-ylmethylcarbamate (35): tert-butyl (S)-1-(N-methoxy methylcarbamoyl)-2 hydroxyethylmethylcarbamate (34) (3.0 g, 11.5 mmol, 1.0 equiv.) was added to a 100 mL RBF followed by DMF (23 mL) and cooled to 0° C. via an ice bath. Next, TBDMSCl (1.9 g, 12.6 mmol, 1.1 equiv.) and imidazole (1.6 g, 23.0 mmol, 2.0 equiv.) were added to the reaction flask. The solution was stirred at 0° C. for 1 h and then allowed to warm to rt, stirring an additional 19 h. The reaction solution was transferred to a 500 mL separatory funnel with EtOAc (150 mL). The mixture was washed with 1% HCl (3×60 mL), sat. NaHCO$_3$ (1×60 mL), and sat. NaCl (2×60 mL). The organic layer was separated and dried over Na$_2$SO$_4$. The solution was concentrated on a rotary evaporator and dried under vacuum to give 4.3 g (98%) of 35 as a colorless oil. The product was found to be 86% ee by chiral HPLC analysis. $R_f$=0.54 (50% EtOAc/hexanes); IR (film) 2954, 2929, 2855, 1702, 1674, 1366, 1153, 1115 cm$^{-1}$; $^1$H NMR (500 MHz, CDCl$_3$) δ Major rotamer: 5.21 (br s, 1H, Boc-N—C$\underline{H}$), 3.84 (m, 2H, CH—C$\underline{H}_2$), 3.70 (s, 3H, N—OC$\underline{H}_3$), 3.13 (s, 3H, N—C$\underline{H}_3$), 1.41 (s, 9H, Boc-t-butyl-C$\underline{H}_3$), 0.82 (s, 9H, Si-t-butyl-C$\underline{H}_3$), 0.01 (s, 6H, Si—(C$\underline{H}_3$)$_2$); Minor rotamer: 4.86 (br s, 1H, Boc-N—C$\underline{H}$), 3.65 (s, 3H, N—OC$\underline{H}_3$), 0.84 (s, 9H, Si-t-butyl-C$\underline{H}_3$); $^{13}$C NMR (125 MHz, CDCl$_3$) δ 171.2, 156.2, 155.6, 80.1, 79.6, 61.7, 61.4, 60.7, 60.2, 57.8, 56.0, 32.2, 31.1, 28.5, 25.8, 18.3, 18.2, −5.4, −5.4. LRMS (ESI-MS m/z): Mass calcd for $C_{17}H_{36}N_2O_5Si$ [M]$^+$, 376.24. Found 377.

Example 34

Tert-butyl 3-(tert-butyldimethylsilyloxy)-1-oxo-1-phenylpropan-2-ylmethylcarbamate (36): tert-butyl 3-(tert-butyldimethylsilyloxy)-1 (methoxy(methyl)amino)-1-oxopropan-2-ylmethylcarbamate (35) (2.2 g, 5.7 mmol, 1.0 equiv.) was added to a 250 mL RBF followed by THF (60 mL). The mixture was cooled to 0° C. via an ice bath and a 1.0 M solution of PhMgBr in THF (11.5 mL, 11.5 mmol, 2.0 equiv.) was added over 5 min. The reaction stirred for 2.25 h at 0° C. and was quenched by addition of 0.5 M HCl (60 mL). The solution was transferred to a separatory funnel with additional 0.5 M HCl (20 mL) and extracted with EtOAc (3×60 mL). The organic layers were combined, washed with sat. NaCl (1×50 mL), and dried over $Na_2SO_4$. The solution was concentrated on a rotary evaporator and dried under vacuum to give 2.8 g of crude material. The residue was purified by flash column chromatography (5% EtOAc/Hexanes) to give 1.5 g (65%) of 36 as an oil. $R_f$=0.23 (5% EtOAc/Hexanes); IR (film) 2954, 2928, 2855, 1687, 1390, 1148, 1120 $cm^{-1}$; $^1H$ NMR (500 MHz, $CDCl_3$) δ Major rotamer: 8.01 (d, J=7.5 Hz, 1H, Ph-H), 7.91 (d, J=7.5 Hz, 1H, Ph-H), 7.55 (t, J=7.0 Hz, 1H, Ph-H), 7.47 (m, 2H, Ph-H), 5.60 (m, 1H, Boc-N—CH), 4.14 (m, 1H, CH—CH$_2$), 4.04 (m, 1H, CH—CH$_2$), 2.75 (s, 3H, Boc-N—CH$_3$), 1.41 (s, 9H, Boc-t-butyl-CH$_3$), 0.90 (s, 9H, Si-t-butyl-CH$_3$), 0.06 (s, 3H, Si—CH$_3$), 0.04 (s, 3H, Si—CH$_3$). Minor rotamer: 5.13 (m, 1H, Boc-N—CH), 2.91 (s, 3H, Boc-N—CH$_3$), 1.43 (s, 9H, Boc-t-butyl-CH$_3$), 0.87 (s, 9H, Si-t-butyl-CH$_3$), 0.08 (s, 3H, Si—CH$_3$), 0.06 (s, 3H, Si—CH$_3$); $^{13}C$ NMR (125 MHz, $CDCl_3$) δ 198.9, 198.1, 155.9, 155.0, 136.1, 133.3, 128.7, 128.6, 128.5, 128.3, 80.9, 80.2, 63.2, 61.1, 60.8, 60.3, 32.7, 31.1, 28.5, 26.0, 25.9, 18.4, 18.3, −5.3, −5.4, −5.5; LRMS (ESI-MS m/z): Mass calcd for $C_{20}H_{33}NO_4Si$ [M]$^+$, 393.59. Found 394.

Example 35

Tert-butyl 3-hydroxy-1-oxo-1-phenylpropan-2-ylmethylcarbamate (37): tertbutyl 3-(tert-butyldimethylsilyloxy)-1-oxo-1-phenylpropan-2-lmethylcarbamate (36) (640 mg, 1.6 mmol, 1.0 equiv.) was added to a 100 mL RBF followed by a 1:1 mixture of THF/$H_2O$ (8 mL). The mixture was stirred and glacial acetic acid (12 mL) was added to the reaction flask. The reaction stirred for 20 h at rt. The reaction was transferred to a 250 mL separatory funnel with sat. NaCl (50 mL) and sat. $NaHCO_3$ (50 mL). The aqueous layer was extracted with EtOAc (3×70 mL) and the combined organic layers were dried over $Na_2SO_4$. The solution was then concentrated on a rotary evaporator and dried under vacuum to give 550 mg of crude material. The residue was purified by flash column chromatography (50% EtOAc/hexanes) to give 440 mg (97%) of 37 as a colorless oil. $R_f$=0.33 (50% EtOAc/hexanes); IR (film) 3451, 2975, 1681, 1149 $cm^{-1}$; $^1H$ NMR (500 MHz, $CDCl_3$) δ Major rotamer: 7.96 (d, J=7.5 Hz, 1H, Ph-H), 7.90 (d, J=7.5 Hz, 1H, Ph-H), 7.58 (t, J=6.5 Hz, 1H, Ph-H), 7.46 (m, 2H, Ph-H), 5.45 (t, J=6.0 Hz, 1H, Boc-N—CH), 4.24 (m, 1H, CH—CH$_2$), 4.14 (m, 1H, CH—CH$_2$), 2.72 (s, 3H, Boc-N—CH$_3$), 2.50 (m, 1H, CH$_2$—OH), 1.43 (s, 9H, Boc-t-butyl-CH$_3$). Minor rotamer: 4.89 (t, J=6.0 Hz, 1H, Boc-N—CH), 3.94 (m, 1H, CH—CH$_2$), 3.81 (m, 1H, CH—CH$_2$), 2.90 (s, 3H, Boc-N—CH$_3$), 1.38 (s, 9H, Boc-t-butyl-CH$_3$); $^{13}C$ NMR (125 MHz, $CDCl_3$) δ 199.9, 199.2, 156.1, 154.6, 135.7, 133.8, 128.9, 128.8, 128.5, 128.3, 81.7, 80.9, 63.5, 61.0, 60.8, 60.7, 33.3, 32.1, 28.4, 28.3; LRMS (ESI-MS m/z): Mass calcd for $C_{15}H_{21}NO_4Na$ [M+Na$^+$], 302.32. Found 302.

Example 36

Tert-butyl-3-oxo-3-phenylpropyl-2-ylmethylcarbamate acetate (38): tertbutyl 3-hydroxy-1-oxo-1-phenylpropan-2-ylmethylcarbamate (37) (390 mg, 1.4 mmol, 1.0 equiv.) was added to a 100 mL RBF followed by $CH_2Cl_2$ (14 mL). The resulting solution was cooled to 0° C. via an ice bath. Next, acetic anhydride (160 mL, 1.7 mmol, 1.2 equiv.), DIEA (300 mL, 1.7 mmol, 1.2 equiv.), and DMAP (17 mg, 0.14 mmol, 0.1 equiv.) were added to the reaction flask. The reaction solution stirred for 15 min at 0° C., was quenched with 1% HCl (25 mL), and transferred to a separatory funnel with $CH_2Cl_2$ (100 mL). The resulting organic layer was washed with 1% HCl (2×50 mL) and sat. NaCl (2×50 mL). The organic layer was dried over $Na_2SO_4$, concentrated on a rotary evaporator, and dried under vacuum to give 440 mg (97%) of 38 as a colorless oil. $R_f$=0.70 (50% EtOAc/hexanes); IR (film) 2975, 1745, 1687, 1390, 1367, 1235, 1148 $cm^{-1}$; $^1H$ NMR (500 MHz, $CDCl_3$) δ Major rotamer: 8.00 (d, J=7.5 Hz, 2H, Ph-CH), 7.92 (d, J=7.5 Hz, 2H, Ph-CH), 7.58 (m, 1H, Ph-CH), 7.46 (m, 2H, Ph-CH), 5.88 (m, 1H, Boc-N—CH), 4.66 (m, 1H, CH—CH$_2$), 4.42 (m, 1H, CH—CH$_2$), 2.66 (s, 3H, Boc-N—CH$_3$), 2.05 (s, 3H, O=C—CH$_3$), 1.45 (s, 9H, t-butyl-CH$_3$); Minor rotamer: 5.42 (m, 1H, Boc-N—CH), 4.60 (m, 1H, CH—CH$_2$), 4.42 (m, 1H, CH—CH$_2$), 2.82 (s, 3H, Boc-N—CH$_3$), 2.09 (s, 3H, O=C—CH$_3$), 1.45 (s, 9H, Boc-t-butyl-CH$_3$); $^{13}C$ NMR (125 MHz, $CDCl_3$) δ 197.5, 196.7, 170.9, 155.9, 154.7, 135.3, 135.1, 133.9, 133.8, 128.9, 128.7, 128.4, 81.4, 80.8, 61.5, 60.7, 59.8, 57.6, 31.7, 30.5, 28.4, 28.4, 21.1, 21.0; LRMS (ESI-MS m/z): Mass calcd for $C_{17}H_{23}NNaO_5Na$ [M+Na]$^+$, 344.36. Found 344.

Example 37

2-(Methylamino)-3-oxo-3-phenylpropyl acetate hydrochloride (16): tert-butyl-3-oxo-3-phenylpropyl-2-ylmethylcarbamate acetate (38) (360 mg, 1.1 mmol, 1.0 equiv.) was added to a 100 mL RBF followed by a 4.0 N HCl-Dioxane solution (8.4 mL, 33.6 mmol, 30 equiv.). The solution was stirred for 15 min and a precipitate formed. $Et_2O$ (50 mL) was added to the reaction flask and the precipitate was filtered with a Buchner funnel. The precipitate was then washed with an additional portion of $Et_2O$ (50 mL) and dried under vacuum to give 280 mg (95%) of 16 as a white solid. Decomposition occurs at 155-160° C.; $^1H$ NMR (500 MHz, DMSO) δ 9.83 (s, 1H, CH—NH$_2$), 9.48 (s, 3H, CH—NH$_2^+$), 8.06 (d, J=7.5 Hz, 2H, Ph-CH), 7.76 (t, J=7.5 Hz, 1H, Ph-CH), 7.59 (t, J=7.5 Hz, 2H, Ph-CH), 5.56 (s, 1H, NH$_2$—CH), 4.68 (dd, J=15.0, 3.0 Hz, 1H, CH—CH$_2$), 4.48 (dd, J=12.5, 3.0 Hz, 1H, CH—CH$_2$), 2.64 (s, 3H, $^+H_2$N—CH$_3$), 1.94 (s, 3H, O=C—CH$_3$); $^{13}C$ NMR (125 MHz, DMSO) δ 193.0, 169.7, 134.8, 133.2, 129.1, 128.8, 61.6, 60.4, 31.3, 20.4; LRMS (ESI-MS m/z): Mass calcd for $C_{12}H_{16}NO_3$ [M]$^+$, 222.26. Found 222. Anal. Calc'd for $C_{12}H_{16}ClNO_3$: C, 55.93; H, 6.26; N, 5.44 Found: C, 55.82; H, 6.20; N, 5.28.

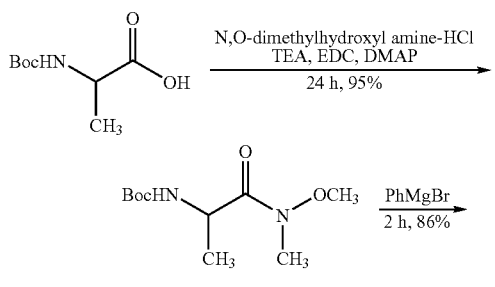

Quaternary Synthesis of 17

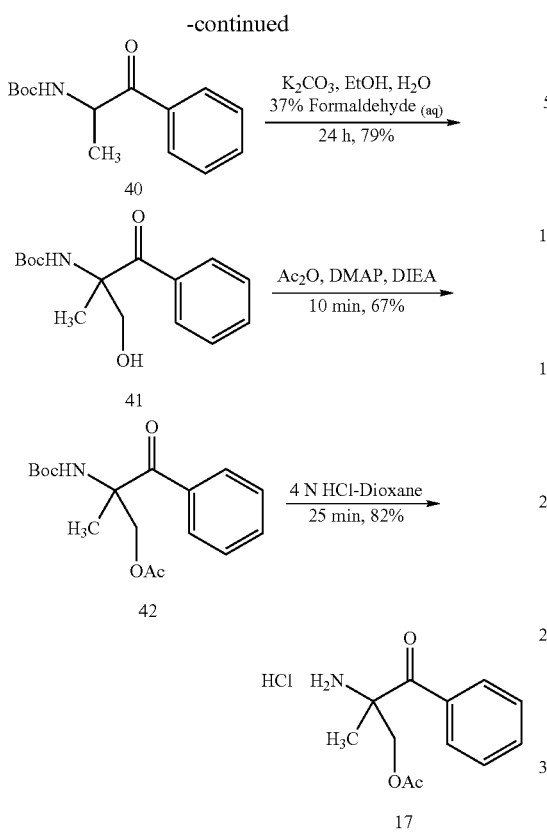

Example 38

Tert-butyl 1-(N-methoxy-N-methylcarbamoyl)ethylcarbamate (39): tert-butyl 1-carboxypropan-2-ylcarbamate (3.8 g, 20.0 mmol, 1.0 equiv.) and N,O-dimethylhydroxyl amine·HCl (2.6 g, 26.1 mmol, 1.33 equiv.) were added to a 250 mL RBF followed by $CH_2Cl_2$ (100 mL). The mixture was cooled to 0° C. via an ice bath and TEA was added (4.7 mL, 33.4 mmol, 1.7 equiv.). Next, EDC (4.6 g, 24.0 mmol, 1.2 equiv.) and DMAP (240 mg, 2.0 mmol, 0.1 equiv.) were added as solids and the solution warmed to rt gradually overnight. After stirring a total of 24 h the reaction solution was transferred to a separatory funnel with $CH_2Cl_2$ (100 mL). The mixture was washed with 1% HCl (2×50 mL), sat. $NaHCO_3$ (1×50 mL), and sat. NaCl (1×50 mL). The organic layer was dried over $Na_2SO_4$, concentrated on a rotary evaporator, and dried under vacuum to give 4.4 g (95%) of 39 as a white solid. mp=150-151° C.; IR (KBr) 3296, 2975, 1705, 1660, 1541, 1296, 1184 cm$^{-1}$; $^1$H NMR (500 MHz, CDCl$_3$) δ 5.30 (br s, 1H, carbamate-NH), 4.73 (br s, 1H, Boc-NH—CH), 3.78 (s, 3H, N—OCH$_3$), 3.19 (s, 3H, N—CH$_3$), 1.44 (s, 9H, Boc-t-butyl-CH$_3$), 1.31 (d, J=6.5 Hz, 3H, CH—CH$_3$); $^{13}$C NMR (125 MHz, CDCl$_3$) δ 173.8, 155.3, 79.6, 61.7, 46.6, 32.2, 28.5, 18.8; LRMS (ESI-MS m/z): Mass calcd for $C_{10}H_{20}N_2NaO_4Si$ [M+Na]$^+$, 232.28. Found 233. Spectroscopic data were consistent with the literature data for this compound.

Example 39

Tert-butyl 1-oxo-1-phenylpropan-2-ylcarbamate (40): tert-butyl 1-(N-methoxy-N-methylcarbamoyl)ethylcarbamate (39) (2.3 g, 10.0 mmol, 1.0 equiv.) was added to a 250 mL RBF followed by THF (100 mL). The mixture was cooled to 0° C. via an ice bath and a 1.0 M solution of PhMgBr in THF (30.0 mL, 30.0 mmol, 3.0 equiv.) was added over 8 min. The reaction stirred for 1.0 h at 0° C. and the ice bath was removed. The reaction stirred for an additional 1.0 h at rt. and was again cooled to 0° C. via an ice bath. Next, the reaction was quenched by addition of 1.0 M HCl (60 mL). The solution was transferred to a separatory funnel with additional 1.0 M HCl (40 mL) and extracted with EtOAc (3×75 mL). The organic layers were combined, washed with sat. NaCl (1×50 mL), and dried over $Na_2SO_4$. The solution was then concentrated on a rotary evaporator and dried under vacuum to give 3.1 g of crude material. The residue was purified by flash column chromatography (15% EtOAc/Hexanes) to give 2.2 g (86%) of 40 as a colorless oil.[10] R$_f$=0.25 (15% EtOAc/Hexanes); IR (film) 3356, 2977, 1680, 1164 cm$^{-1}$; $^1$H NMR (500 MHz, CDCl$_3$) δ 7.96 (d, J=7.5 Hz, 2H, Ph-H), 7.59 (t, J=7.5 Hz, 1H, Ph-H), 7.48 (t, J=7.5 Hz, 2H, Ph-H), 5.62 (br d, J=6.5 Hz, 1H, carbamate-NH), 5.30 (t, 1H, Boc-NH—CH), 3.78 (s, 3H, N—OCH$_3$), 3.19 (s, 3H, N—CH$_3$), 1.46 (s, 9H, Boc-t-butyl-CH$_3$, 1.40 (d, J=7.0 Hz, 3H, CH—CH$_3$); $^{13}$C NMR (125 MHz, CDCl$_3$) δ 199.6, 155.5, 134.3, 133.9, 129.0, 128.8, 80.0, 51.3, 28.6, 20.1; LRMS (ESI-MS m/z): Mass calcd for $C_{14}H_{19}NO_3$ [2M]$^+$, 498.62. Found 499. Spectroscopic data were consistent with the literature data for this compound.

Example 40

Tert-butyl 3-hydroxy-2-methyl-1-oxo-1-phenylpropan-2-ylcarbamate (41): tert-butyl 1-oxo-1-phenylpropan-2-ylcarbamate (40) (1.3 g, 5.0 mmol, 1.0 equiv.) was added to a 100 mL RBF followed by EtOH (39 mL). Next, a 37% solution of formaldehyde (8.1 mL, 100 mmol, 20.0 equiv.) was added to the reaction mixture and the solution heated to 35° C. Finally, a 0.5 M solution of $K_2CO_3$ (350 mg, 2.5 mmol, 5.0 mL d$H_2O$, 0.5 equiv.) was added to the reaction flask and the solution stirred vigorously for 24 h. The solution was neutralized with 1% HCl, transferred to a separatory funnel with a 1.7 M solution of NaCl (5.0 g, 85.0 mmol, 50 mL $H_2O$), and extracted with $CH_2Cl_2$ (5×50 mL). The organic layers were combined and dried over $Na_2SO_4$. The resulting solution was concentrated on a rotary evaporator and dried under vacuum to give a crude oil. The residue was purified by flash column chromatography (30% EtOAc/Hexanes) to give 1.1 g (79%) of 41 as a colorless oil. R$_f$=0.29 (50% EtOAc/Hexanes); IR (film) 3352, 2977, 1684, 1367, 1166 cm$^{-1}$; $^1$H NMR (500 MHz, CDCl$_3$) δ Major Rotamer: 8.00 (br s, 2H, Ph-H), 7.42 (br s, 3H, Ph-H), 5.87 (br s, 1H, carbamate-NH), 5.49 (br s, 1H, Boc-NH—CH), 4.12 (m, 2H, C—CH$_2$), 3.76 (m, 2H, C—CH$_2$), 3.32 (br s, 2H, CH$_2$—OH), 1.63 (s, 3H, C—CH$_3$), 1.26 (s, 9H, t-butyl-CH$_3$). Minor Rotamer: 8.15 (br s, 2H, Ph-H), 7.51 (br s, 3H, Ph-H), 5.82 (br s, 1H, carbamate-NH), 3.09 (br s, 2H, CH$_2$—OH), 1.09 (s, 9H, t-butyl-CH$_3$); $^{13}$C NMR (125 MHz, CDCl$_3$) Major Rotamer: δ 202.8, 155.1, 132.9, 128.5, 128.3, 80.5, 67.9, 64.4, 28.2, 21.6; LRMS (ESI-MS m/z): Mass calcd for $C_{15}H_{21}NNaO_4$ [M+Na]$^+$, 302.32. Found 302.

Example 41

2-(Tert-butoxycarbonyl)-2-methyl-3-oxo-3-phenylpropyl acetate (42): tert-butyl 3-hydroxy-2-methyl-1-oxo-1-phenylpropan-2-ylcarbamate (41) (560 mg, 2.0 mmol, 1.0 equiv.) was added to a 100 mL RBF followed by $CH_2Cl_2$ (20 mL). The resulting solution was cooled to 0° C. via an ice bath. Next, acetic anhydride (250 µL, 2.6 mmol, 1.3 equiv.), DIEA (420 µL, 2.4 mmol, 1.2 equiv.), and DMAP (24 mg, 0.1 mmol, 0.05 equiv.) were added to the reaction flask. The reaction solution stirred for 10 min at 0° C., was quenched with 1% HCl (25 mL), and transferred to a separatory funnel with $CH_2Cl_2$ (80 mL). The resulting organic layer was washed with 1% HCl (2×20 mL) and sat. NaCl (2×30 mL). The organic layer was dried over $Na_2SO_4$, concentrated on a rotary evaporator, and dried under vacuum to give a crude oil. The residue was purified by flash column chromatography (40% EtOAc/Hexanes) to give 430 mg (67%) of 42 as a colorless oil which crystallized to a white solid upon standing. $R_f$=0.36 (50% EtOAc/Hexanes); mp=95-97° C.; IR (KBr) 3408, 2979, 1725, 1703, 1680, 1505, 1257, 1161 $cm^{-1}$; $^1H$ NMR (500 MHz, $CDCl_3$) δ Major Rotamer: 8.01 (br s, 2H, Ph-$\underline{H}$), 7.42 (br s, 3H, Ph-$\underline{H}$), 5.52 (br s, 1H, carbamate-N$\underline{H}$), 4.65 (m, 1H, C—C$\underline{H}_2$), 4.49 (m, 1H, C—C$\underline{H}_2$), 2.11 (s, 3H, O=C—C$\underline{H}_3$), 1.64 (s, 3H, C—C$\underline{H}_3$), 1.25 (s, 9H, t-butyl-C$\underline{H}_3$). Minor Rotamer: 8.18 (br s, 2H, Ph-$\underline{H}$), 7.51 (m, 3H, Ph-$\underline{H}$), 5.93 (br s, 1H, carbamate-N$\underline{H}$), 1.11 (s, 9H, t-butyl-C$\underline{H}_3$); $^{13}C$ NMR (125 MHz, $CDCl_3$) δ 199.9, 198.9, 170.8, 154.2, 135.8, 134.7, 132.9, 132.2, 129.0, 128.4, 128.2, 81.8, 80.2, 67.3, 66.9, 62.9, 28.2, 27.7, 22.7, 21.7, 21.0; LRMS (ESI-MS m/z): Mass calcd for $C_{17}H_{23}NNaO_5$ $[M+Na]^+$, 344.36. Found 344.

Example 42

2-Amino-2-methyl-3-oxo-3-phenylpropyl acetate hydrochloride (17): 2-(tert-butoxycarbonyl)-2-methyl-3-oxo-3-phenylpropyl acetate (42) (270 mg, 0.8 mmol, 1 equiv.) was added to a 100 mL RBF followed by a 4.0 N HCl-Dioxane solution (6.3 mL, 25.0 mmol, 30 equiv.). The solution was stirred for 25 min and half of the dioxane was evaporated with a steady stream of $N_2$ $_{(g)}$. $Et_2O$ (25 mL) was added to the reaction flask and a white precipitate formed. Additional $Et_2O$ (25 mL) was added and the mixture was filtered with a Buchner funnel. The precipitate was then washed with an additional portion of $Et_2O$ (30 mL) and dried under vacuum to give 180 mg (82%) of 17 as a white solid. mp=166-168° C.; $^1H$ NMR (500 MHz, DMSO) δ 8.97 (s, 3H, C—N$\underline{H}_3$) 7.97 (d, J=8.0 Hz, 2H, Ph-$\underline{H}$), 7.69 (t, J=8.0 Hz, 1H, Ph-$\underline{H}$), 7.55 (t, J=8.0 Hz, 2H, Ph-$\underline{H}$), 4.79 (d, J=12.5 Hz, H, C—C$\underline{H}_2$), 4.68 (d, J=12.5 Hz, 1H, C—C$\underline{H}_2$), 1.93 (s, 3H, O=C—C$\underline{H}_3$), 1.76 (s, 3H, C—C$\underline{H}_3$); $^{13}C$ NMR (125 MHz, DMSO) δ 196.5, 169.5, 133.6, 133.3, 129.0, 128.7, 65.9, 64.2, 20.4 19.4; LRMS (ESI-MS m/z): Mass calcd for $C_{16}H_{16}NO_3$ $[M]^+$, 222.26. Found 222. Anal. calcd for $C_{12}H_{16}ClNO_3$: C, 55.93; H, 6.26; N, 5.43 Found: C, 55.76; H, 6.36; N, 5.23.

Example 43

Figure 7:
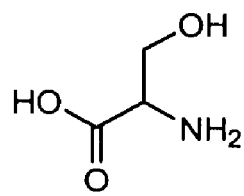
FIG. 7 illustrates a generalized synthetic pathway, from serine, for generating alternate compounds for reactivating mutant p53, in accordance with the present invention.
Figure 7:
Figure 7:
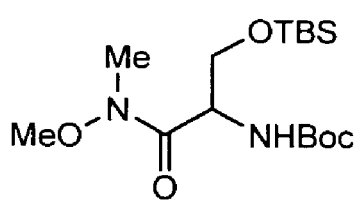
Figure 7:
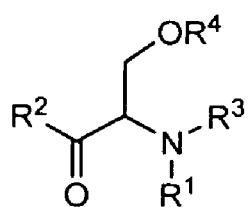

Generally, transformation from serine (D- or L-) to numerous compounds of this invention can proceed by reaction with a Grignard (or alkyllithium) reagent (see, Scheme 1, above and FIG. 7). Because compound 22 contains a Weinreb amide, this reaction allows control over the $R^2$ position in the final compound. (See, e.g., example 46b and comparative use of several phenyl-substituted derivatives.) Deprotection of the t-butyldimethylsilyl (TBS)-protected alcohol using tetrabutylammonium fluoride (TBAF) will afford a primary hydroxyl group that can be acylated or alkylated, providing control of the group at $R^4$. Finally, deprotection of the t-butoxycarbonyl (Boc)-protected nitrogen with trifluoroacetic acid (TFA) will give a free amine that can be alkylated or acylated to control the groups at $R^1$ and $R^3$. Since there are large numbers of Grignard, alkyllithium, alkylating, and acylating reagents available, there are an enormous number of different structures that are represented by the final compound represented in FIG. 7. In comparison to the synthesis of PRIMA-1, a synthetic route of the type described herein allows examination of the effects of many different functional groups in the greatest number of positions—a strategy to yield classes of molecules that can be optimized for activity with different versions of mutant p53 that come from different cancer cells.

Example 44

Compound 7 is resynthesized via the route outlined in FIG. 7 to determine whether one enantiomer of compound 7 is more active than the other. As shown, the primary amine in compound 7 is converted to a series of secondary and tertiary amines, through choice of alkylation or acylation reagent, that bear more resemblance to the nitrogen in PRIMA-1. Once useful groups for positions $R^1$ and $R^3$ are determined, the groups at positions $R^2$ and $R^4$ can be varied.

Example 45

Figure 8:
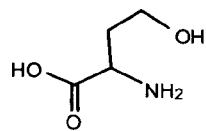
FIG. 8 shows additional starting materials, for use analogous to the syntheses of FIG. 7, to probe the effects of sidechain lengths and other heteroatoms (e.g., nitrogen vs. oxygen) on the mechanism of reactivating mutant p53, consistent with the methodology of the present invention.
Figure 8:
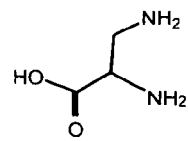
Figure 8:
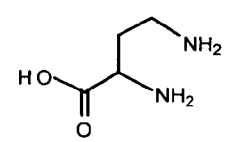

Side chain modification is possible, as would be understood by those skilled in the art—without undue experimentation—as provided herein or using straight forward modifications of known techniques. For instance, starting from D- or L-homoserine, diaminopropionic acid, or diaminobutyric acid (FIG. 8) and using the synthetic procedures outlined in FIG. 7 and provided elsewhere herein, the effects of lengthening the sidechain, and replacing the sidechain oxygen with a nitrogen can be examined. With analysis of appropriate R group substitution, different aspects of combinatorial chemistry are applied to expand the diversity of the target molecules and, thus, speed up the rate at which analogs of these molecules can be synthesized to generate libraries of compounds that can be screened against different forms of mutant p53.

Example 46a

Cellular growth studies were performed on Saos2 cells. Human osteosarcoma Saos2 cells are devoid of endogenous p53 due to biallelic deletion of the p53 gene. Previously, a series of Saos2 cell lines were engineered to express several human p53 mutants that are commonly found in human cancers. The derivative Saos2 cell lines used in the present study included the following: 1) Saos2-CMV, which is the vector-only control cell line that is negative for p53 protein. 2) Saos2-175, which expresses the human mutant p53-R175H protein. The 175H substitution disrupts the structure of the protein resulting in the loss of DNA binding and tumor suppressor function. This mutation is found in ~6% of all cancers of diverse tumor types. 3) Saos2-273, which expressed the human mutant p53-R273H protein. The 273H substitution eliminates a DNA contact point resulting in the loss of DNA binding and tumor suppressor function. This mutation represents the second most common hot spot mutation and is found in nearly 8% of all cancers. 4) Saos2-281, which expresses the human mutant p53-D281G protein. This mutation disrupts a stabilizing salt bridge resulting in the loss of DNA binding and tumor suppressor function.

The cells were grown at 37° C. in Dulbecco's modified Eagle's medium (Cambrex, East Rutherford, N.J.) supplemented with 10% fetal bovine serum (Hyclone, Logan, Utah) under 5% $CO_2$. The cells were plated at $1 \times 10^6$ per 10 cm tissue culture plates and treated with escalating doses of the indicated compounds (Table 1) for varying lengths of time. Routine concentrations of the synthesized compounds ranged from 1-75 μM. After 72-96 hours, the cells were refed with fresh medium containing the appropriate concentration of the compound. In addition, parallel cultures were prepared and maintained under identical conditions without drug treatment as negative controls. The cells were microscopically analyzed during the course of treatment and the overall effectiveness of the drug treatment on cell growth and survival was assessed on day 7 by staining the cells with Giemsa Stain GS500 (SIGMA, St. Louis, Mo.). Prima-1 was included in all experiments for comparison purposes. As shown in the figure below, compound 7 efficiently and selectively inhibited the growth of the Saos2 cell lines expressing mutant p53, either by inducing cell death and/or cell cycle arrest, while having no effect on the CMV-only cells which lack p53 protein. The few Saos2 mutant p53 cells remaining after treatment with compound 7 were quite large and flat, reminiscent of a differentiated cell.

Example 46b

Cellular growth studies were also performed through treatment with several phenyl-substituted derivatives of compound 8. Using protocols described above, cells were treated with the p-fluorophenyl-, p-methoxyphenyl- and p-methylphenyl-derivatives of the (S)-enantiomer. Such compounds and other derivatives can be prepared from the corresponding Grignard (or alkylithium) reagent in reaction with a Weinreb amide. (See, e.g., intermediate 22 and subsequent reaction thereof, in Scheme 1.) As above, such compounds selectively inhibited growth of cell lines expressing mutant p53.

Example 47 p53 DNA Binding Assays: Active compound 4 and derivative compounds thereof in the restoration of DNA binding function to mutant p53. To assess this property, p53 is prepared as RIPA lysates from Saos-1 and (10)3 cells and analyzed by Electromobility Shift Assays (EMSA) as previously described (Gu et al., 1996). Specifically, synthetic double-strand oligonucleotides useful in this study are known in the art and include: p53CON, p53RE, and p53MRE. The probes are radiolabeled with [g-32P]ATP and T4 polynucleotide kinase. As a positive control, the probes are incubated with 100 ng of baculovirus-expressed human p53 protein (>95% pure) alone or together with 2 mg of PAb421 (Oncogene Research Products, Cambridge, Mass.) in binding buffer containing 20 mM HEPES (pH 7.9), 25 mM KCl, 0.1 mM EDTA, 2 mM MgCl2, 0.5 mM dithiothreitol, 0.25% Nonidet P-40, 2 mM spermidine, 10% glycerol, 0.1 ng bovine and 0.04 mg poly[dG-dC] at 22° C. for 15 min. Lysates containing no p53 or mutant p53 from vehicle-only or compound 2 treated cells are analyzed by EMSA in parallel. The protein-DNA complexes are resolved in a native 4% polyacrylamide gel and analyzed by autoradiography.

Example 48

The effect of compound 4 derivatives are also addressed in vitro by adding the compounds to baculovirus purified mutant p53 proteins. Mutant p53 is unable to bind DNA in a sequence specific manner and therefore is unable to shift the probe unless compound 4 and derivative compounds are competent for restoring wild-type p53 biochemical properties.

P53 Transactivation Assays:

(a) Promoter-reporter studies Promoter-reporter studies rely on the wild-type p53-responsive promoter-luciferase reporter construct (50-2 Luc), which has been described previously (Zambetti et al., 1993). The wild-type p53-responsive reporter contains the luciferase gene under the transcriptional control of the adenovirus major late TATA box and terminal deoxynucleotidyl-transferase initiator element. Upstream of this minimal promoter are two copies of the p53 response element from the murine muscle creatine kinase gene, both of which are arranged in the forward orientation. The (10)1 cells are transiently transfected with 250 ng of the 50-2 Luc reporter construct by the calcium phosphate method. Cells are then treated with compound 4 or its derivatives and after varying time intervals are harvested, protein extracts prepared and quantified, and equal amounts of protein used in a standard luciferase assay (Promega Corp, Madison, Wis.). Prima-1 reactivates wild-type p53 function in cells expressing mutant p53, which results in an increase in CAT expression from 50-2 Luc reporter, but not the parental vector lacking the p53 consensus sites. By contrast, no increase in CAT expression is observed in Prima-1-treated cells lacking mutant p53. Active compound 4 and its derivative compounds are believed to restore wild-type p53 function and lead to a selective increase in CAT expression only in cells expressing mutant p53.

(b) Endogenous target gene expression studies compound 4 and derivative compounds that reactivate mutant p53 should result in an increase in expression of endogenous genes that are normally regulated by wild-type p53, such as p21Cip1, Puma and Mdm2. To assess the effectiveness of compound 4 and derivative compounds, the Saos-2 and (10)3 cells described above are treated with drug for varying time intervals, washed and harvested. Total RNA is prepared using the RNeasy Mini Kit as recommended by the manufacturer (Qiagen, Valencia, Calif.). The RNA samples (10 ug) are denatured in 1 M glyoxal-10 mM NaH2PO4 [pH 7.0] for one hour at 50° C. and resolved through a 1.2% agarose gel. The RNA samples are transferred to a Zeta-Probe Blotting Membrane (Bio-Rad) in transfer buffer containing 10 mM NaCl. The membrane is blocked in hybridization solution (1 mM EDTA, 0.25 M Na2HPO4 [pH 7.2] and 7% SDS) for 5 min and hybridized with [32P]-radiolabeled DNA probes for 16 hours in fresh hybridization solution at 65° C. The membrane is washed twice at 65° C. for 30 min per wash in buffer I (1 mM EDTA, 40 mM Na2HPO4 [pH 7.2] and 5% SDS) followed by two washes in buffer II (1 mM EDTA, 40 mM Na2HPO4 [pH 7.2] and 1% SDS). Target gene expression is quantitated by Phosphorimager analysis using Imagequant Software. Zambetti G, Bargonetti J, Walker K, Prives C, Levine A. Wild-type p53 mediates positive regulation of gene expression through a specific DNA sequence element. Genes Dev 6:1143-1152, 1992. Gu Z, Flemington C, Jenkins N A, Copeland N G, Chittenden T, Zambetti, G P. EI24: A p53 response gene involved in growth suppression and apoptosis. Mol Cell Biol 18:3735-3743, 2000.

What is claim is:

1. A tumor suppressor reactivator compound of a formula

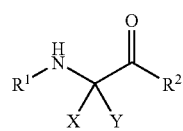

wherein $R^1$ is H; $R^2$ is selected from phenyl and substituted phenyl moieties; X is selected from hydroxymethyl and acetoxymethyl; and Y is acetoxymethyl; and salts thereof.

2. The compound of claim 1 wherein $R^2$ is phenyl.

3. The compound of claim 2 wherein said phenyl moiety is halo-substituted.

4. The compound of claim 1 wherein X is acetoxymethyl.

5. The compound of claim 1 wherein X is hydroxymethyl.

6. The compound of claim 5 selected from the (R)-enantiomer, the (S)-enantiomer and a racemic mixture thereof.

7. The compound of claim 1 wherein said compound is an ammonium salt and the counter ion is the conjugate base of a protic acid.

* * * * *

UNITED STATES PATENT AND TRADEMARK OFFICE
CERTIFICATE OF CORRECTION

| | | |
|---|---|---|
| PATENT NO. | : 7,329,775 B2 | Page 1 of 1 |
| APPLICATION NO. | : 10/978702 | |
| DATED | : February 12, 2008 | |
| INVENTOR(S) | : Daniel H. Appella and Michael C. Myers | |

It is certified that error appears in the above-identified patent and that said Letters Patent is hereby corrected as shown below:

Column 1, Lines 6-10:

"The United States government has certain rights to this invention pursuant to Grant Nos. CA63230, CA71907 and CA21765 from the National Institutes of Health to Northwestern University." should be -- This invention was made with government support under Grant Numbers CA063230, CA071907 and CA021765 awarded by the National Institutes of Health. The government has certain rights in the invention. --

Col. 1, Line 51 "(PFTA)" should be -- (PFTα) --;

Col. 24, Line 38 "$^1$H NMR" should be -- 1H NMR --;

Col. 31, Line 34 "lmethylcarbamata" should be -- ylmethylcarbamata --;

Col. 35, Line 43 "H" should be -- 1H --;

Col. 38, Line 2 "Promoter-reporter studies Promoter-reporter studies" should be -- Promoter-reporter studies --.

Signed and Sealed this

Thirteenth Day of September, 2011

David J. Kappos
*Director of the United States Patent and Trademark Office*